United States Patent
Chambon et al.

(10) Patent No.: US 9,115,102 B2
(45) Date of Patent: *Aug. 25, 2015

(54) N-[2-HYDROXYCARBAMOYL-2-(PIPERAZINYL) ETHYL] BENZAMIDE COMPOUNDS, THEIR PREPARATION AND THEIR USE AS TACE INHIBITORS

(75) Inventors: Sandrine Chambon, Le Cannet (FR); Laurence Clary, La Colle sur Loup (FR); Marlene Schuppli, Le Rouret (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 611 days.

This patent is subject to a terminal disclaimer.

(21) Appl. No.: 13/496,637

(22) PCT Filed: Sep. 16, 2010

(86) PCT No.: PCT/EP2010/063594
§ 371 (c)(1),
(2), (4) Date: Mar. 23, 2012

(87) PCT Pub. No.: WO2011/033009
PCT Pub. Date: Mar. 24, 2011

(65) Prior Publication Data
US 2012/0178934 A1 Jul. 12, 2012

Related U.S. Application Data

(60) Provisional application No. 61/272,369, filed on Sep. 17, 2009.

(30) Foreign Application Priority Data

Sep. 17, 2009 (FR) ..................... 09 56376

(51) Int. Cl.
*C07D 295/26* (2006.01)
*A61K 31/495* (2006.01)
*C07D 209/12* (2006.01)
*C07D 211/22* (2006.01)
*C07D 213/30* (2006.01)
*C07D 215/14* (2006.01)
*C07D 231/12* (2006.01)
*C07D 233/02* (2006.01)
*C07D 307/79* (2006.01)
*C07D 401/12* (2006.01)
*C07D 471/04* (2006.01)

(52) U.S. Cl.
CPC ............ *C07D 295/26* (2013.01); *C07D 209/12* (2013.01); *C07D 211/22* (2013.01); *C07D 213/30* (2013.01); *C07D 215/14* (2013.01); *C07D 231/12* (2013.01); *C07D 233/02* (2013.01); *C07D 307/79* (2013.01); *C07D 401/12* (2013.01); *C07D 471/04* (2013.01)

(58) Field of Classification Search
None
See application file for complete search history.

(56) References Cited

U.S. PATENT DOCUMENTS

| 8,420,632 B2 * | 4/2013 | Clary et al. ............... 514/218 |
| 8,633,196 B2 * | 1/2014 | Clary et al. ............. 514/253.06 |
| 2004/0072802 A1 | 4/2004 | Duan et al. |

FOREIGN PATENT DOCUMENTS

| JP | 2002-535383 A | 10/2002 |
| WO | 0044711 A1 | 8/2000 |
| WO | WO-02/30873 A1 | 4/2002 |
| WO | 2008045671 A1 | 4/2008 |

OTHER PUBLICATIONS

Patani. Chemical Reviews, 1996, vol. 96, No. 8, pp. 3147-3176.*
Lin. Clinical Immunology, 2008, 126, 13-30.*
Yokota et al., "MMP/ADAM Inhibitors. Therapeutic Potential for Psoriasis", Expect Opinion on Therapeutic Patents, vol. 15, No. 4, Jan. 1, 2005, pp. 421-435, XP002402629.
International Preliminary Report on Patentability and Written Opinion of the International Searching Authority dated Mar. 20, 2012 issued in corresponding Application No. PCT/EP2010/063594.
Duan et al., "Discovery of β-benzamido hydroxamic acids as potent, selective, and orally bioavailable TACE inhibitors," Bioorganic & Medicinal Chemistry Letters, 2008, 18, pp. 241-246.

* cited by examiner

*Primary Examiner* — Noble Jarrell
(74) *Attorney, Agent, or Firm* — Dentons US LLP

(57) ABSTRACT

The present invention relates to novel benzene-carboxamide compounds having a structure that corresponds to the general formula (I), and also to their method of synthesis and to their use in pharmaceutical compositions intended for use in human or veterinary medicine or else to their use in cosmetic compositions.

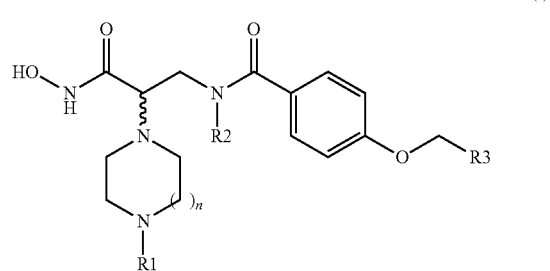

23 Claims, No Drawings

N-[2-HYDROXYCARBAMOYL-2-(PIPERAZINYL) ETHYL] BENZAMIDE COMPOUNDS, THEIR PREPARATION AND THEIR USE AS TACE INHIBITORS

CROSS REFERENCE TO RELATED APPLICATIONS

This application is a National Phase filing under 35 U.S.C. §371 of PCT/EP2010/063594 filed on Sep. 16, 2010; and this application claims priority to Application No. 0956376 filed in France on Sep. 17, 2009 under 35 U.S.C. §119; and claims the benefit of U.S. Provisional Application No. 61/272,369 filed Sep. 17, 2009. The entire contents of each of these applications is hereby incorporated by reference.

TECHNICAL FIELD

The present invention relates to novel benzene-carboxamide compounds corresponding to the general formula (I) below:

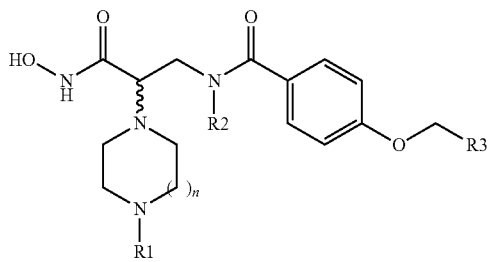

and also to their method of synthesis and to their use in pharmaceutical compositions intended for use in human or veterinary medicine.

The compounds of the present invention act as inhibitors of the TNFα-converting enzyme, also known as TACE. Therefore, they are of use in the treatment of diseases for which reducing the production of TNFα is of great benefit.

The present invention also relates to the use of compounds corresponding to the general formula (I) in cosmetic compositions.

PRIOR ART

Adamalysins ("ADAMs" or A Disintegrin and Metalloproteinase) are a sub-family of zinc metalloendopeptidase enzymes. Their ectodomain comprises a protease domain, the activation of which depends on the zinc, a disintegrin domain and a cysteine-rich domain. To date, at least 30 different ADAMs have been identified, the first one of which to be characterized was ADAM17, also known as TACE (TNFα-converting enzyme) [Gueydan C et al. Med. Sci 1997, 13, 83-88; Black R. A et al. Nature 1997, 385:729-733; Moss et al. Nature 1997, 385:733-736]. TACE mRNA is present in numerous tissues and more particularly in monocytes, macrophages, T lymphocytes but also in keratinocytes for example.

TACE is responsible for the cleavage of pro-TNFα, a 26 kDa membrane protein, in order to result in the release of soluble TNFα, a biologically active 17 kDa protein [Schlondorff et al. Biochem. J. 2000, 347, 131-138]. The soluble TNFα released by the cell is capable of acting on sites very far from the site of synthesis. TNFα is involved in a large number of pro-inflammatory biological processes [Aggarwal et al, Eur. Cytokine Netw., 1996, 7: 93-124]. Several pharmacological and clinical studies have clearly shown that blocking the effects of TNFα with specific antibodies or anti-TNFα biological agents (Etanercept, Adalimumab, Infliximab) was beneficial in the treatment of autoimmune diseases such as rheumatoid arthritis [Feldman et al., Lancet, 1994, 344, 1105), non-insulin-dependent diabetes mellitus [Lohmander L. S. et al., Arthritis Rheum, 1993, 36, 1214-1222], and Crohn's disease [MacDonald et al., Clin. Exp. Immunol. 1990, 81, 301].

TNFα also plays a fundamental role during the inflammatory phenomenon triggered in psoriasis lesions. The serum TNFα levels are high in psoriatic patients [Mussi A et al. J. Biol. Regul. Homeost Agents, 1997, 11, 115-118]; the TNFα levels are also high in the actual psoriatic plaques [Bonifati C. et al. Clin. Exp. Dermatol., 1994, 19, 383-387]. The key cells in the physiopathology of psoriasis are the keratinocytes, the dendritic cells and certain T lymphocytes. The interaction between these families of cells results in an inflammatory cascade leading to the lesions characteristic of psoriasis with release of TNFα[Kupper T S, N. Engl. J. Med, 2003, 349, 1987-1990]. Clinical studies for the treatment of moderate to severe plaque psoriasis by anti-TNFα biological agents (Etanercept, Adalimumab, Infliximab) demonstrated their effectiveness both on psoriatic lesions and on the quality of life of the patients [Ortonne J P, Annales de dermatologie et de vénéreologie, 2005, 132 (8-9 pt2), 4S6-9 and 2005, 132, 9501-9S70].

Thus, compounds which inhibit the production of TNFα are of great benefit for the treatment of inflammatory diseases and diseases involving release of TNFα.

SUMMARY OF THE INVENTION

Our invention therefore describes novel molecules which inhibit the TACE enzyme (TNFα-converting enzyme) and therefore inhibit the secretion of soluble TNFα (active form of TNFα) by cells. These novel molecules are therefore potential active principles for the treatment of pathologies that involve a reduction or an inhibition of TNFα production.

By way of illustration, and non-limitingly, these pathologies are, for example, septic shock, haemodynamic shock, malaria, inflammatory bowel diseases (IBDs) such as Crohn's disease and ulcerative colitis, inflammatory bone diseases, mycobacterium infections, meningitis, fibrotic diseases, heart diseases, ischaemic attack, graft rejection, cancer, atherosclerosis, obesity, diseases involving angiogenesis phenomena, autoimmune diseases, osteoarthritis, rheumatoid arthritis, ankylosing spondylitis, chronic juvenile arthritis, multiple sclerosis, HIV, non-insulin-dependent diabetes mellitus, allergic diseases, asthma, chronic obstructive pulmonary disease (COPD), ocular inflammation, inflammatory diseases of the skin, psoriasis, atopic dermatitis and psoriatic arthritis.

These molecules are also potential active principles for the treatment of neurological pathologies having an inflammatory nature, for which reducing the production of TNFα would be of great benefit. These pathologies listed below in a non-limiting manner are, for example, Alzheimer's disease, Parkinson's disease, Parkinsonian disorders, amyotrophic lateral sclerosis, autoimmune diseases of the nervous system, autonomic diseases of the nervous system, dorsal pains, cerebral oedema, cerebrovascular diseases, dementia, nerve fibre demyelinating autoimmune diseases of the nervous system, diabetic neuropathies, encephalitis, encephalomyelitis, epilepsy, chronic fatigue syndrome, giant cell arteritis, Guillain- Barré syndrome, headaches, multiple sclerosis, neuralgia, peripheral nervous system diseases, polyneuropathies, polyradiculoneuropathy, radiculopathy, respiratory paralyses, spinal cord diseases, Tourette syndrome, central nervous system vasculitis, Huntington's disease and cerebral attack.

A large variety of TACE inhibitors are already known as indicated below. However, a large number of these inhibitors do not act selectively on the TACE enzyme relative to other enzymes from the family of ADAMs and/or matrix metalloproteinases (MMPs).

However, the non-selective inhibition of these families of enzymes induces undesirable side effects observed in vivo. For example, the inhibition of MMP-1 (collagenase-1) has been associated with musculoskeletal toxicity problems.

As a non-selective inhibitor, mention may also be made of Apratastat, a known inhibitor tested in phase 2 clinical trials for the treatment of rheumatoid arthritis (Curr Opin Investig Drugs. 2006 November; 7(11), 1014-1019). This inhibitor is not selective for the TACE enzyme compared to certain MMPs (WO 00/44709; page 251, table 10, example 61).

Certain cyclic β-amido hydroxamic derivatives have already been described in WO 99/37625, WO 00/044730, WO 03/055856 and EP 01/301989 as matrix metalloproteinase inhibitors and/or TACE inhibitors. Other patents (WO 98/15525, WO 00/059874, WO 02/030873) claim non-cyclic amide derivatives as inhibitors of matrix metalloproteinases and/or of TNFα and/or of aggrecanase. Other non-cyclic β-amido hydroxamic derivatives are described as antibacterial agents in patents WO 04/062601 and WO 08/154,642. Patent WO 01/070734 claims, in a very broad general structure, β-amino acid derivatives as inhibitors of matrix metalloproteases and of TNFα, without presenting biological results on the TACE enzyme.

However, the applicant has now discovered, unexpectedly and surprisingly, that novel compounds of general formula (I) have a very good TACE-inhibiting activity and in particular inhibit the TACE enzyme selectively relative to other ADAMs and MMPs.

Thus, the present invention relates to compounds of general formula (I) below:

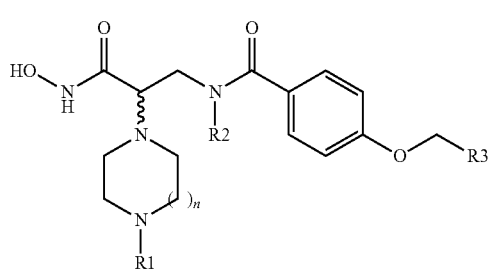

(I)

in which:
$R_1$ represents a hydrogen, an alkyl radical, a substituted alkyl radical, an alkenyl radical, a substituted alkenyl radical, an alkynyl radical, a substituted alkynyl radical, an aralkyl radical, a substituted aralkyl radical, a heteroaralkyl radical, a substituted heteroaralkyl radical, a —C(O)—$R_4$ radical, an —$SO_2$—$R_4$ radical or a C(O)O$R_4$ radical, $R_4$ having the meanings given below;

$R_2$ is a hydrogen atom or a lower alkyl radical;
$R_3$ is an alkyl radical, a substituted alkyl radical, an alkenyl radical, a substituted alkenyl radical, an alkynyl radical, a substituted alkynyl radical, an aryl radical, a substituted aryl radical, an aralkyl radical, a substituted aralkyl radical, a heterocyclic radical, a substituted heterocyclic radical, a cycloalkyl radical, a substituted cycloalkyl radical, a heteroaryl radical, a substituted heteroaryl radical, a heteroaralkyl radical or a substituted heteroaralkyl radical;
$R_4$ is an alkyl radical, a substituted alkyl radical, an alkenyl radical, a substituted alkenyl radical, an alkynyl radical, a substituted alkynyl radical, an aryl radical, a substituted aryl radical, an aralkyl radical or a substituted aralkyl radical;
n may take the values of 0, 1, 2 or 3;
and also the addition salts of the compounds of general formula (I) with a pharmaceutically acceptable acid, the addition salts of the compounds of general formula (I) with a pharmaceutically acceptable base and the enantiomers of the compounds of general formula (I).

Among the addition salts of the compounds of general formula (I) with a pharmaceutically acceptable acid, mention may preferably be made of the salts with an organic acid or with an inorganic acid.

Suitable inorganic acids are, for example, hydrohalic acids such as hydrochloric acid and hydrobromic acid, sulphuric acid, nitric acid and phosphoric acid.

Suitable organic acids are, for example, acetic acid, trifluoroacetic acid, trichloroacetic acid, propionic acid, glycolic acid, pyruvic acid, succinic acid, benzoic acid, cinnamic acid, mandelic acid, methanesulphonic acid, para-toluenesulphonic acid, salicylic acid, picric acid, citric acid, oxalic acid, tartaric acid, malonic acid, maleic acid, camphorsulphonic acid and fumaric acid.

Among the addition salts of the compounds of general formula (I) with a pharmaceutically acceptable base, mention may preferably be made of the salts with an organic base or with an inorganic base.

Suitable inorganic bases are the hydroxides of alkali metals or of alkaline-earth metals or carbonates of alkali metals or of alkaline-earth metals. Among these bases, mention may be made, for example, of potassium hydroxide, sodium hydroxide, lithium hydroxide, calcium hydroxide, potassium carbonate, sodium carbonate and calcium carbonate.

Suitable organic bases include amines and amino acids. Among the amines, mention may be made, for example, of aliphatic or aromatic primary, secondary or tertiary amines such as methylamine, ethylamine, ethanolamine, propylamine, isopropylamine, the 4 isomers of butylamine, dimethylamine, diethylamine, diethanolamine, dipropylamine, diisopropylamine, di-n-butylamine, pyrrolidine, piperidine, morpholine, diethanolphenylamine, trimethylamine, triethylamine, tripropylamine, quinuclidine, pyridine, quinoline and isoquinoline.

Among the amino acids, mention may be made, for example, of lysine, arginine and ornithine.

According to the present invention, the expression "lower alkyl radical" denotes a linear or branched saturated hydrocarbon-based chain comprising from 1 to 4 carbon atoms.

According to the present invention, the expression "alkyl radical" denotes a linear or branched saturated hydrocarbon-based chain comprising from 1 to 10 carbon atoms.

According to the present invention, the expression "alkenyl radical" denotes a linear or branched unsaturated hydrocarbon-based chain comprising from 2 to 10 carbon atoms and comprising one or more double bonds.

According to the present invention, the expression "alkynyl radical" denotes a linear or branched unsaturated hydrocarbon-based chain comprising from 2 to 10 carbon atoms and comprising one or more triple bonds.

According to the present invention, the expression "substituted alkyl radical" denotes a linear or branched saturated hydrocarbon-based chain comprising from 1 to 10 carbon atoms and substituted with one or more radicals chosen from a halogen atom, an alkoxy radical and a hydroxyl radical.

According to the present invention, the expression "substituted alkenyl radical" denotes a linear or branched unsaturated hydrocarbon-based chain comprising from 2 to 10 carbon atoms, comprising one or more double bonds and substituted with one or more radicals chosen from a halogen atom, an alkoxy radical and a hydroxyl radical.

According to the present invention, the expression "substituted alkynyl radical" denotes a linear or branched unsaturated hydrocarbon-based chain comprising from 2 to 10 carbon atoms, comprising one or more triple bonds and substituted with one or more radicals chosen from a halogen atom, an alkoxy radical and a hydroxyl radical.

According to the present invention, the term "cycloalkyl" denotes a cyclic saturated hydrocarbon-based chain comprising from 3 to 7 carbon atoms.

According to the present invention, the expression "substituted cycloalkyl" denotes a cyclic saturated hydrocarbon-based chain comprising from 3 to 7 carbon atoms and substituted with one or more radicals chosen from a halogen atom, an alkoxy radical and a hydroxyl radical.

According to the present invention, the expression "aryl radical" denotes an aromatic hydrocarbon-based ring or two fused aromatic hydrocarbon-based rings.
The preferred aryl radicals are chosen from phenyl and naphthyl radicals.

According to the present invention, the expression "substituted aryl radical" denotes an aromatic hydrocarbon-based ring or two fused aromatic hydrocarbon-based rings substituted with one or more groups of atoms chosen from an alkyl, an alkoxy, an aryl, a halogen, a hydroxyl, a cyano, a trifluoromethyl and a nitro.

According to the present invention, the expression "aralkyl radical" denotes an alkyl substituted with an aryl.

According to the present invention, the expression "substituted aralkyl radical" denotes an alkyl substituted with a substituted aryl.

According to the present invention, the expression "heterocyclic radical" denotes a saturated or unsaturated, cyclic or polycyclic hydrocarbon-based chain comprising one or more heteroatoms chosen from O, S and N.

According to the present invention, the expression "substituted heterocyclic radical" denotes a heterocyclic radical substituted with one or more groups of atoms chosen from an alkyl, an alkoxy, a halogen, a hydroxyl, a cyano, a trifluoromethyl and a nitro.

According to the present invention, the expression "heteroaryl radical" denotes an aromatic heterocyclic radical, that is to say an aromatic, cyclic or polycyclic, hydrocarbon-based chain comprising one or more heteroatoms chosen from O, S and N.

According to the present invention, the expression "substituted heteroaryl radical" denotes a heteroaryl radical substituted with one or more groups of atoms chosen, for example, from an alkyl, an alkoxy, an aryl, a substituted aryl, a halogen, a hydroxy, a cyano, a trifluoromethyl and a nitro.

According to the present invention, the expression "heteroaralkyl radical" denotes an alkyl radical substituted with a heteroaryl radical.

According to the present invention, the expression "substituted heteroaralkyl radical" denotes a heteroaralkyl radical substituted with one or more groups of atoms chosen from an alkyl, an alkoxy, a halogen, a hydroxyl, a cyano, a trifluoromethyl and a nitro.

According to the present invention, the expression "alkoxy radical" denotes an oxygen atom substituted with an alkyl radical.

According to the present invention, the expression "halogen atom" denotes a fluorine, chlorine, bromine or iodine atom.

Among the compounds of general formula (I) that fall within the scope of the present invention, mention may especially be made of the following compounds:

1) 4-but-2-ynyloxy-N-[2-hydroxycarbamoyl-2-(4-methanesulphonylpiperazin-1-yl)ethyl]benzamide
2) 4-but-2-ynyloxy-N—[(S)-2-hydroxycarbamoyl-2-(4-methanesulphonylpiperazin-1-yl)ethyl]benzamide
3) 4-but-2-ynyloxy-N—[(R)-2-hydroxycarbamoyl-2-(4-methanesulphonylpiperazin-1-yl)ethyl]benzamide
4) N—[(S)-2-hydroxycarbamoyl-2-(4-methanesulphonylpiperazin-1-yl)ethyl]-4-methoxybenzamide
5) 4-cyclopropylmethoxy-N—[(S)-2-hydroxycarbamoyl-2-(4-methanesulphonylpiperazin-1-yl)ethyl]benzamide
6) 4-benzyloxy-N—[(S)-2-hydroxycarbamoyl-2-(4-methanesulphonylpiperazin-1-yl)ethyl]benzamide
7) 4-butoxy-N—[(S)-2-hydroxycarbamoyl-2-(4-methanesulphonylpiperazin-1-yl)ethyl]benzamide
8) 4-but-2-ynyloxy-N-{(S)-2-hydroxycarbamoyl-2-[4-(toluene-4-sulphonyl)piperazin-1-yl]ethyl}-benzamide
9) 4-(4-fluorobenzyloxy)-N—[(S)-2-hydroxycarbamoyl-2-(4-methanesulphonylpiperazin-1-yl)ethyl]-benzamide hydrochloride
10) N—[(S)-2-hydroxycarbamoyl-2-(4-methanesulphonylpiperazin-1-yl)ethyl]-4-(4-trifluoromethyl-benzyloxy) benzamide
11) N—[(S)-2-hydroxycarbamoyl-2-(4-methanesulphonylpiperazin-1-yl)ethyl]-4-(4-methylbenzyloxy)-benzamide
12) [(S)-2-hydroxycarbamoyl-2-(4-methanesulphonylpiperazin-1-yl)ethyl]-2,3-dihydrobenzofuran-5-carboxamide
13) 4-but-2-ynyloxy-N—[(S)-2-hydroxycarbamoyl-2-(4-methanesulphonylpiperazin-1-yl)ethyl]-N-methylbenzamide
14) N—[(S)-2-hydroxycarbamoyl-2-(4-methanesulphonylpiperazin-1-yl)ethyl]-4-(2-methylquinolin-4-yl-methoxy)benzamide
15) N—[(S)-2-hydroxycarbamoyl-2-(4-methanesulphonylpiperazin-1-yl)ethyl]-4-(naphthalen-1-yl-methoxy) benzamide 16) 4-(4-hydroxybut-2-ynyloxy)-N—[(S)-2-hydroxycarbamoyl-2-(4-methanesulphonylpiperazin-1-yl)-ethyl]benzamide
17) N—[(S)-2-hydroxycarbamoyl-2-(4-methanesulphonylpiperazin-1-yl)ethyl]-4-(4-methoxybenzyloxy)-benzamide
18) N—[(S)-2-hydroxycarbamoyl-2-(4-methanesulphonylpiperazin-1-yl)ethyl]-4-(pyridin-4-ylmethoxy)-benzamide
19) N—[(S)-2-hydroxycarbamoyl-2-(4-methanesulphonylpiperazin-1-yl)ethyl]-4-(2-methylnaphthalen-1-ylmethoxy)benzamide
20) N—[(R)-2-hydroxycarbamoyl-2-(4-methanesulphonylpiperazin-1-yl)ethyl]-4-(2-methylquinolin-4-yl-methoxy)benzamide
21) N—[(S)-2-hydroxycarbamoyl-2-(4-methanesulphonylpiperazin-1-yl)ethyl]-4-(quinolin-4-ylmethoxy)-benzamide
22) N—[(S)-2-(4-benzylpiperazin-1-yl)-2-hydroxycarbamoylethyl]-4-(2-methylquinolin-4-yl-methoxy)benzamide
23) N-{(S)-2-hydroxycarbamoyl-2-[4-(propane-2-sulphonyl)piperazin-1-yl]ethyl}-4-(2-methylquinolin-4-yl-methoxy)benzamide
24) N—[(S)-2-hydroxycarbamoyl-2-(4-methanesulphonylpiperazin-1-yl)ethyl]-4-(2-methylquinolin-4-yl-methoxy)benzamide dihydrochloride
25) N—[(S)-2-(4-ethylpiperazin-1-yl)-2-hydroxycarbamoylethyl]-4-(2-methylquinolin-4-ylmethoxy)-benzamide
26) N-{(S)-2-[4-(4-fluorobenzyl)piperazin-1-yl]-2-hydroxycarbamoylethyl}-4-(2-methylquinolin-4-yl-methoxy)benzamide
27) N—[(S)-2-(4-benzylpiperazin-1-yl)-2-hydroxycarbamoylethyl]-4-(2-trifluoromethylpyrazolo[1,5-a]pyridin-3-ylmethoxy)benzamide
28) N-{(S)-2-hydroxycarbamoyl-2-[4-(propane-2-sulphonyl)piperazin-1-yl]ethyl}-4-(1-methylpiperidin-4-yl-methoxy)benzamide
29) N—[(S)-2-hydroxycarbamoyl-2-(4-isobutyryl-piperazin-1-yl)ethyl]-4-(2-methylpyridin-4-yl-methoxy)-N-propylbenzamide
30) N—[(S)-2-(3-benzylimidazolidin-1-yl)-2-hydroxycarbamoylethyl]-4-(2,6-dimethylpyridin-4-yl-methoxy)benzamide
31) N—[(S)-2-hydroxycarbamoyl-2-(3-methanesulphonylimidazolidin-1-yl)ethyl]-4-(3-methylbenzyloxy)-benzamide
32) N—[(S)-2-hydroxycarbamoyl-2-(4-methanesulphonyl-[1,4]diazepan-1-yl)ethyl]-4-(2-methylquinolin-4-yl-methoxy)benzamide
33) N—((S)-2-[1,4]diazepan-1-yl-2-hydroxycarbamoylethyl)-4-(quinolin-4-ylmethoxy)benzamide
34) 4-(2-cyclopropylquinolin-4-ylmethoxy)-N-{(S)-2-hydroxycarbamoyl-2-[4-(propane-2-sulphonyl)-piperazin-1-yl]ethyl}benzamide
35) 4-(2-cyclopropylpyridin-4-ylmethoxy)-N—[(S)-2-(4-ethyl[1,4]diazocan-1-yl)-2-hydroxycarbamoyl-ethyl]-benzamide
36) N—[(S)-2-hydroxycarbamoyl-2-(4-isobutyryl-[1,4]diazocan-1-yl)ethyl]-4-(2-methylpyrazolo-[1,5-a]pyridin-3-ylmethoxy)benzamide
37) N—[(S)-2-hydroxycarbamoyl-2-(4-methanesulphonylpiperazin-1-yl)ethyl]-4-(2-trifluoromethylpyrazolo[1,5-a]pyridin-3-ylmethoxy)benzamide
38) N—[(S)-2-(4-benzenesulphonylpiperazin-1-yl)-2-hydroxycarbamoylethyl]-4-(3-methyl-1H-pyrazol-4-yl-methoxy)benzamide
39) N—[(R)-2-(4-benzoylpiperazin-1-yl)-2-hydroxycarbamoylethyl]-4-(piperidin-4-ylmethoxy)-benzamide
40) N—[(S)-2-hydroxycarbamoyl-2-(4-isobutyryl-piperazin-1-yl)ethyl]-4-(2-methylquinolin-4-yl-methoxy)benzamide
41) N-{(S)-2-hydroxycarbamoyl-2-[4-(propane-2-sulphonyl)piperazin-1-yl]ethyl}-4-(2-methyl-1H-indol-3-yl-methoxy)benzamide and
42) N—[(S)-2-(4-benzylpiperazin-1-yl)-2-hydroxycarbamoylethyl]-4-(2-isopropylbenzofuran-3-yl-methoxy)benzamide.

The compounds of general formula (I) are prepared according to the reaction scheme (Scheme 1) presented below.

Scheme 1

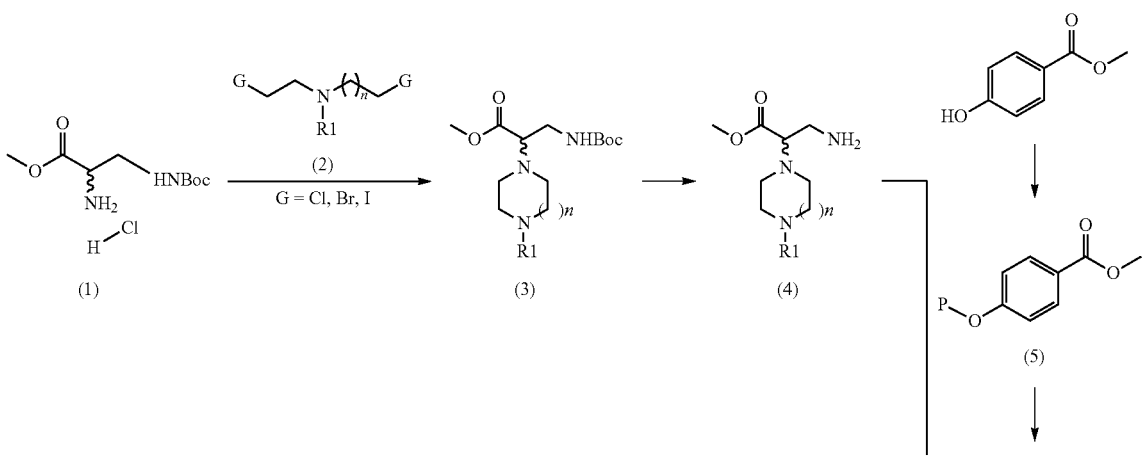

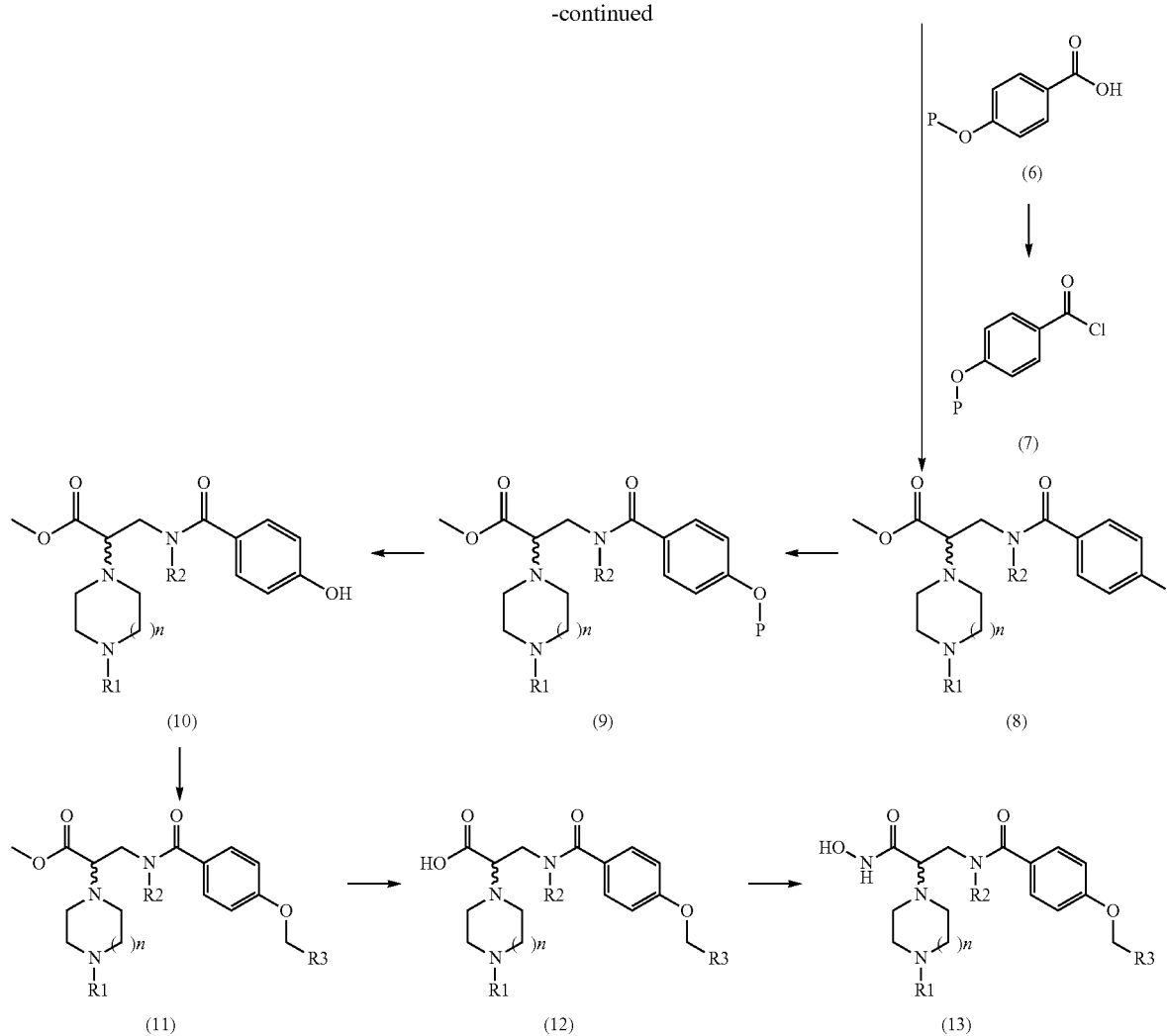

According to Scheme 1, the compounds (3) are obtained by a reaction between the amino acid (1) H-DAP(Boc)-OMe-.HCl or H-(D)-DAP(Boc)-OMe.HCl and the compound (2) (commercial or previously prepared) in the presence of a tertiary organic base such as diiso-propylethylamine or tri-ethylamine at a temperature between 60° C. and 120° C. The compounds (4) are obtained by deprotection of the amine functional group of the compounds (3) according to conventional methods such as, for example, the use of a solution of hydrochloric acid in isopropanol.

By protecting the methyl 4-hydroxybenzoate by reaction with benzyl bromide, for example in the presence of a base such as potassium carbonate in a solvent such as 2-butanone, the compound (5) is obtained. After saponification of the compound (5) in order to lead to the derivative (6), a reaction with oxalyl chloride in the presence of dimethylformamide in dichloromethane for example leads to the derivative (7).

A reaction between the compound (4) and the 4-hydroxybenzoyl chloride O-protected by a benzyl group for example (P=$CH_2$-Ph) (7) in the presence of a tertiary base such as, for example, triethylamine in dichloromethane leads to the compound (8). N-alkylation of the amide functional group may then be carried out by reaction with an alkyl halide in the presence of a base such as, for example, sodium hydride in a solvent such as DMF in order to lead to the derivative (9). The compound (10) is obtained by deprotection according to methods known to a person skilled in the art for deprotecting a phenol functional group. The compound (11) is obtained by alkylation of the phenol functional group of the compound (10) by reaction with an alkyl halide in the presence of a base such as, for example, caesium carbonate in acetone or by Mitsunobu reaction with a primary alcohol derivative in the presence of triphenylphosphine and diisopropylazodicar-boxylate for example. Via a saponification reaction in the presence of a base such as lithium hydroxide in the presence of water and tetrahydrofuran, the compound (12) is obtained. In a last step, the compound (13) is obtained by coupling between the 0-(tert-butyldimethyl-silyl)hydroxylamine for example and the derivative (12) under conventional peptide coupling conditions, using, for example, as coupling agents, 1-(3-dimethylamino-propyl)-3-ethylcarbodiimide hydrochloride, hydroxybenzotriazole or TBTU and, as a base, triethylamine or diisopropylethylamine in a solvent such as dichloromethane or dimethylformamide. The deprotection of the silylated hydroxamic acid intermediately formed takes place in situ or by washing with an acid aqueous solution in order to result in the compound (13).

Another alternative for obtaining the compound (13) is presented in Scheme 2 below.

Scheme 2

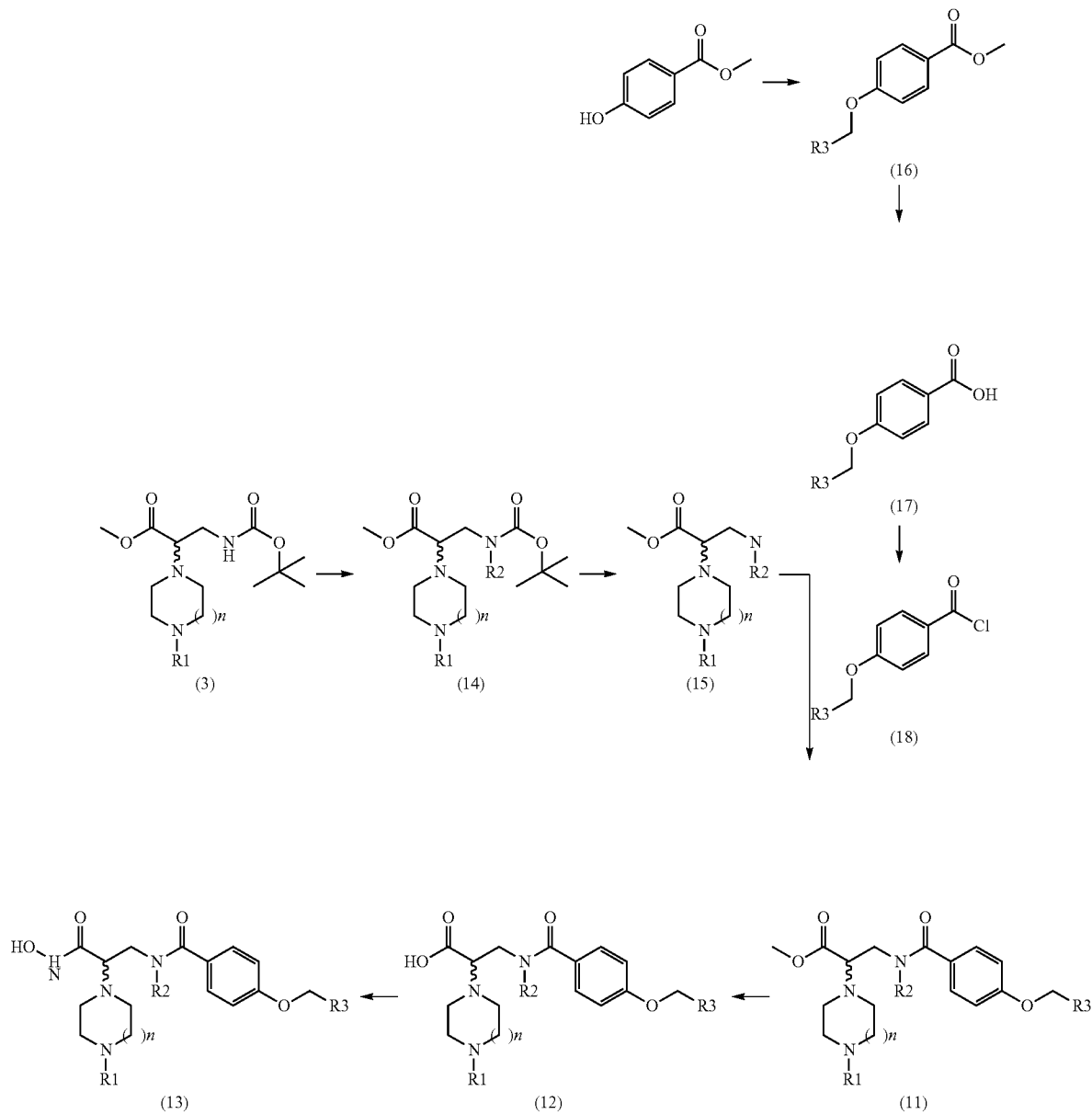

According to the synthesis scheme from Scheme 2, the derivative (3) may optionally be alkylated in the presence of a base such as sodium hydride and of an alkyl halide in dimethylformamide for example to result in the compound (14) from which the compound (15) is obtained according to conventional methods for the deprotection of amines such as, for example, the use of a solution of hydrochloric acid in isopropanol.

Via alkylation of methyl 4-hydroxybenzoate with an alkyl halide in the presence of a base such as potassium carbonate for example in a solvent such as 2-butanone, the compound (16) is obtained. After saponification of the compound (16) in order to result in the derivative (17), a reaction with oxalyl chloride in the presence of dimethylformamide in dichloromethane for example results in the derivative (18).

The derivative (11) is obtained by a reaction between the compounds (15) and (18) in the presence of a base such as triethylamine in dichloromethane for example. The compound (13) is then obtained from the derivative (11) according to the same reaction pathway as that presented in Scheme 1.

An alternative synthetic pathway for obtaining the compound (13) is also presented in Scheme 3 below.

Scheme 3

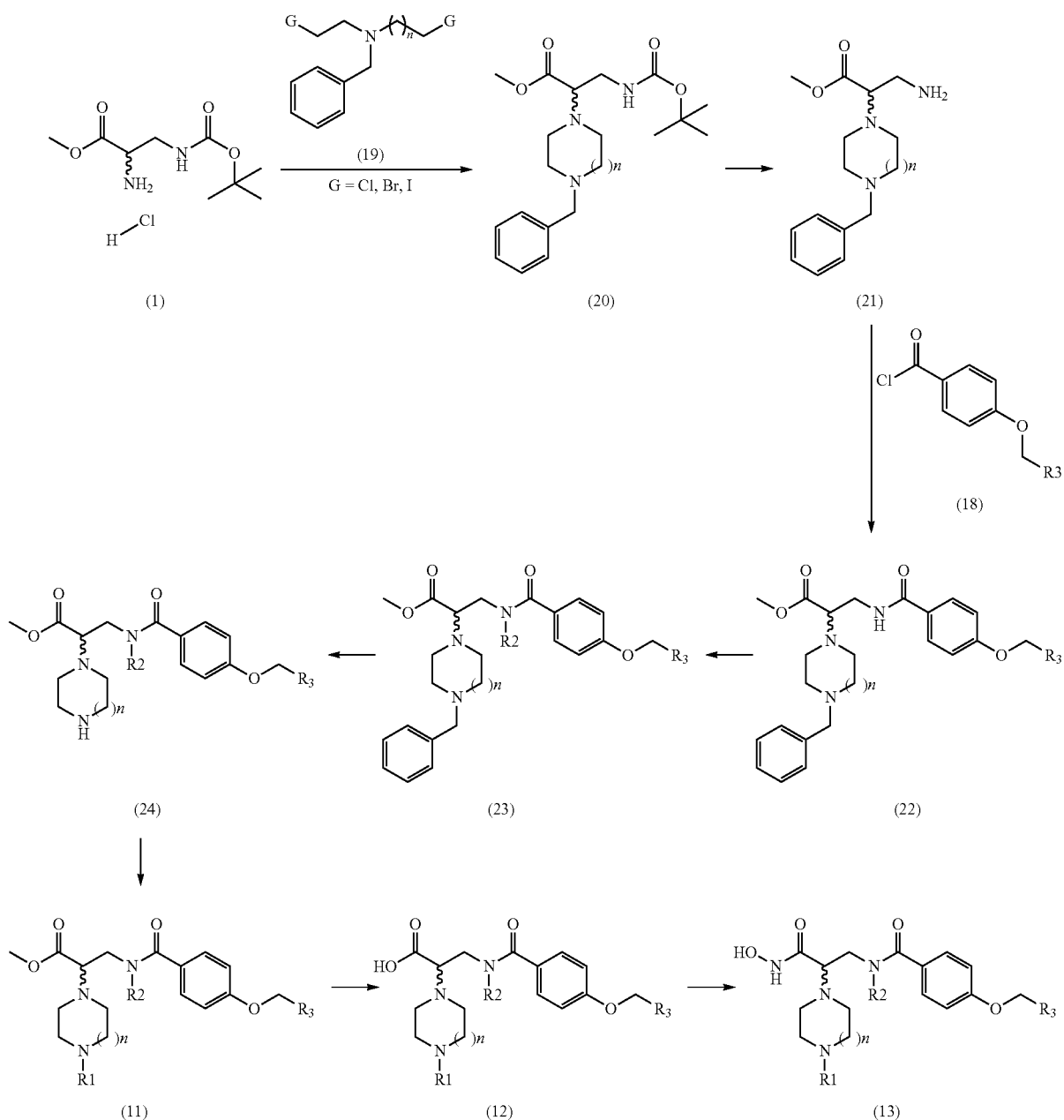

According to Scheme 3, the compound (20) is obtained by reaction between the amino acid (1) H-DAP(Boc)-OMe.HCl or H-(D)-DAP(Boc)-OMe.HCl and the compound (19) (previously prepared by reaction of bis(2-chloroethyl)amine for example and benzyl bromide in the presence of potassium carbonate in acetonitrile) in the presence of a tertiary organic base such as diisopropylethylamine at a temperature of approximately 120° C. After deprotection of the amine functional group, the compound (21) is condensed with benzoyl chloride (18) in order to result in the derivative (22). N-alkylation of the amide functional group may then be carried out by reaction with an alkyl halide in the presence of a base such as, for example, sodium hydride in a solvent such as DMF in order to result in the derivative (23). Under the conventional conditions of hydrogenation of the compound (23) in the presence of palladium on carbon in a solvent such as ethanol for example, the compound (24) is obtained. The compound (11) is obtained according to conventional methods of synthesis for example by reaction of the compound (24) with an acyl chloride, or a sulphonyl chloride in the presence of triethylamine, or by reaction with an alkyl halide in the presence of a base such as sodium hydride for example. The compound (13) is then obtained from the derivative (11) according to the same reaction pathway as that presented in Schemes 1 and 2.

An alternative synthetic pathway for the compounds with R1 representing a —(CO)—R4 radical is described in Scheme 4.

Scheme 4

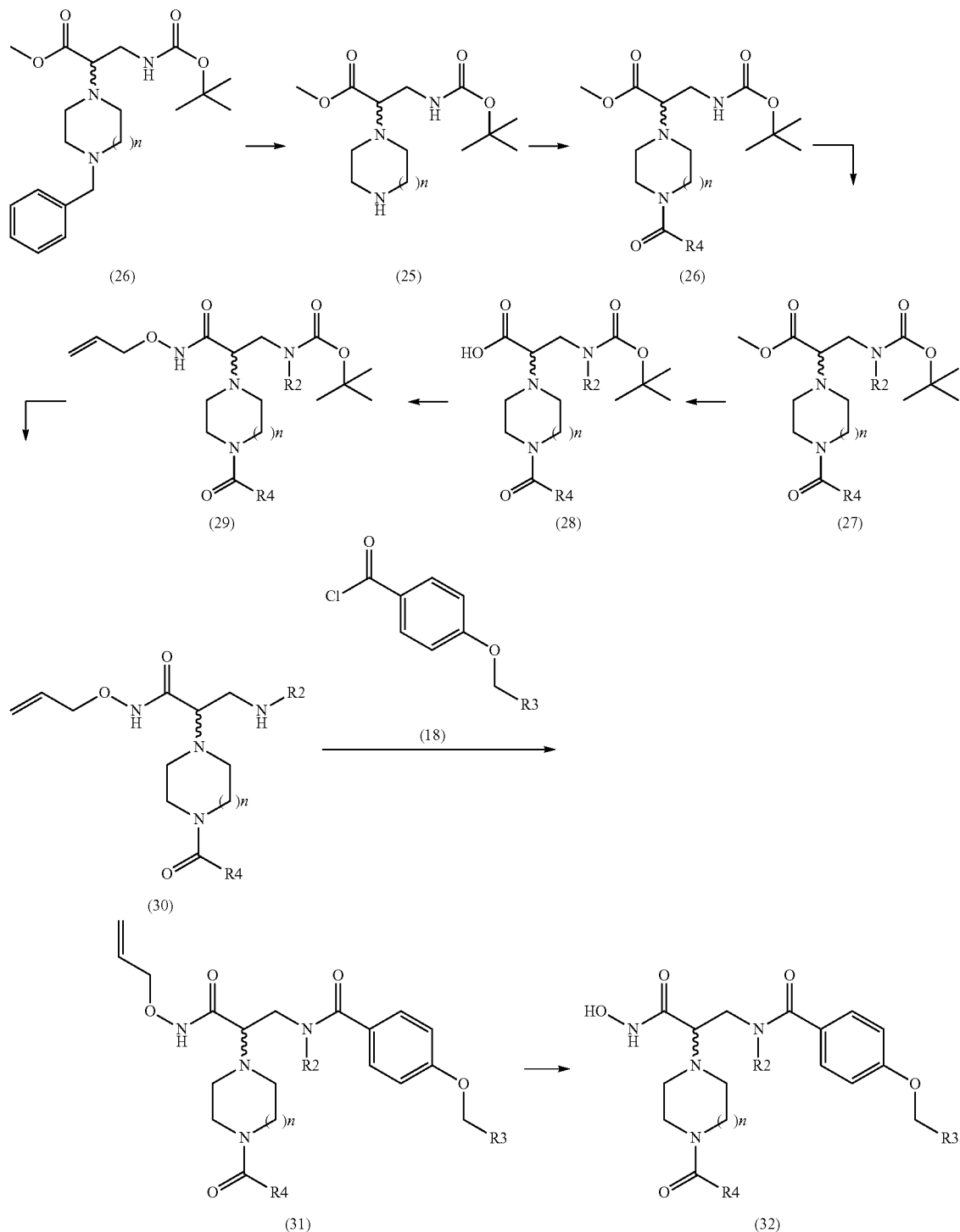

After deprotection of the amine functional group of the compound (20) according to conventional hydrogenation conditions in the presence of palladium on carbon in a solvent such as ethanol for example, the compound (25) is obtained. By reaction with an acyl chloride, R₄COCl in the presence of a base such as triethylamine, the compound (26) is obtained. When R₂ represents a lower alkyl radical, N-alkylation of the carbamate is then carried out by reaction with an alkyl halide in the presence of a base such as, for example, sodium hydride in a solvent such as DMF in order to result in the derivative (27). By saponification reaction in the presence of a base such as lithium hydroxide in the presence of water and of tetrahydrofuran for example, the compound (28) is prepared. A coupling between O-allylhydroxylamine hydrochloride for example and the derivative (28) makes it possible to obtain the compound (29) under conventional peptide coupling conditions. For this, use is made, for example, of 1-(3-dimethylaminopropyl)-3-ethylcarbodiimide hydrochloride, hydroxybenzotriazole or TBTU as coupling agents, and triethylamine or diisopropylethylamine as base. The reaction takes place in a solvent such as dichloromethane or dimethylformamide. After deprotection of the amine functional group of the compound (29) according to conventional methods, the compound (30) is obtained. It is condensed with benzoyl chloride (18) in order to result in the compound (31). In a last step, the compound (32) is obtained by deprotection of the hydroxylamine functional group of the compound (31) according to conventional methods such as, for example, treatment with tetrakis(triphenylphosphine)palladium(0) and potassium carbonate in methanol.

According to the present invention, the compounds of general formula (I) that are preferred are those for which:

$R_1$ represents a hydrogen, an alkyl radical, a substituted alkyl radical, an alkenyl radical, a substituted alkenyl radical, an alkynyl radical, a substituted alkynyl radical, an aralkyl radical, a substituted aralkyl radical, a heteroaralkyl radical, a substituted heteroaralkyl radical, a —C(O)—$R_4$ radical, a —SO$_2$—$R_4$ radical or a C(O)O$R_4$ radical, $R_4$ having the meanings given below;

$R_2$ is a hydrogen atom or a lower alkyl radical;

$R_3$ is an alkyl radical, a substituted alkyl radical, an alkenyl radical, a substituted alkenyl radical, an alkynyl radical, a substituted alkynyl radical, an aryl radical, a substituted aryl radical, an aralkyl radical, a substituted aralkyl radical, a heterocyclic radical, a substituted heterocyclic radical, a heteroaryl radical, a substituted heteroaryl radical, a heteroaralkyl radical or a substituted heteroaralkyl radical;

$R_4$ is an alkyl radical, a substituted alkyl radical, an alkenyl radical, a substituted alkenyl radical, an alkynyl radical, a substituted alkynyl radical, an aryl radical, a substituted aryl radical, an aralkyl radical or a substituted aralkyl radical;

n may take the values of 0, 1 or 2;

and also their addition salts with a pharmaceutically acceptable acid, their addition salts with a pharmaceutically acceptable base and the enantiomers of said compounds.

According to the present invention, the compounds of general formula (I) that are particularly preferred are those for which:

$R_1$ represents a hydrogen, an alkyl radical, a substituted alkyl radical, an alkenyl radical, a substituted alkenyl radical, an alkynyl radical, a substituted alkynyl radical, an aralkyl radical, a substituted aralkyl radical, a —C(O)—$R_4$ radical or an —SO$_2$—$R_4$ radical, $R_4$ having the meanings given below;

$R_2$ is a hydrogen atom or a lower alkyl radical;

$R_3$ is an alkyl radical, a substituted alkyl radical, an alkenyl radical, a substituted alkenyl radical, an alkynyl radical, a substituted alkynyl radical, an aryl radical, a substituted aryl radical, an aralkyl radical, a substituted aralkyl radical, a heterocyclic radical, a substituted heterocyclic radical, a heteroaryl radical, a substituted heteroaryl radical, a heteroaralkyl radical or a substituted heteroaralkyl radical;

$R_4$ is an alkyl radical, a substituted alkyl radical, an aryl radical, a substituted aryl radical, an aralkyl radical or a substituted aralkyl radical;

n may take the values of 1 or 2;

and also their addition salts with a pharmaceutically acceptable acid, their addition salts with a pharmaceutically acceptable base and the enantiomers of said compounds.

According to the present invention, the compounds of general formula (I) that are more particularly preferred are those for which:

$R_1$ represents an alkyl radical, a substituted alkyl radical, an aralkyl radical, a substituted aralkyl radical, a —C(O)—$R_4$ radical or an —SO$_2$—$R_4$ radical, $R_4$ having the meanings given below;

$R_2$ is a hydrogen atom;

$R_3$ is an alkynyl radical, a substituted alkynyl radical, an aryl radical, a substituted aryl radical, an aralkyl radical, a substituted aralkyl radical, a heterocyclic radical, a substituted heterocyclic radical, a heteroaryl radical, a substituted heteroaryl radical, a heteroaralkyl radical or a substituted heteroaralkyl radical;

$R_4$ is an alkyl radical, a substituted alkyl radical, an aryl radical, a substituted aryl radical, an aralkyl radical or a substituted aralkyl radical;

n takes the value of 1;

and also their addition salts with a pharmaceutically acceptable acid, their addition salts with a pharmaceutically acceptable base and the enantiomers of said compounds.

According to the present invention, the compounds of general formula (I) that are even more particularly preferred are those for which:

$R_1$ represents an alkyl radical, a substituted alkyl radical, an aralkyl radical, a substituted aralkyl radical, a —C(O)—$R_4$ radical or an —SO$_2$—$R_4$ radical, $R_4$ having the meanings given below;

$R_2$ is a hydrogen atom;

$R_3$ is an alkynyl radical, a substituted alkynyl radical, a heterocyclic radical, a substituted heterocyclic radical, a heteroaryl radical, a substituted heteroaryl radical, a heteroaralkyl radical or a substituted heteroaralkyl radical;

$R_4$ is an alkyl radical, a substituted alkyl radical, an aryl radical, a substituted aryl radical, an aralkyl radical or a substituted aralkyl radical;

n takes the value of 1;

and also their addition salts with a pharmaceutically acceptable acid, their addition salts with a pharmaceutically acceptable base and the enantiomers of said compounds.

According to the present invention, the compounds of general formula (I) that are most particularly preferred are those for which:

$R_1$ represents an alkyl radical, a substituted alkyl radical, an aralkyl radical, a substituted aralkyl radical, a —C(O)—$R_4$ radical or an —SO$_2$—$R_4$ radical, $R_4$ having the meanings given below;

$R_2$ is a hydrogen atom;

$R_3$ is an alkynyl radical, a substituted alkynyl radical, a heteroaryl radical or a substituted heteroaryl radical;

$R_4$ is an alkyl radical, a substituted alkyl radical, an aryl radical, a substituted aryl radical, an aralkyl radical or a substituted aralkyl radical;

n takes the value of 1;

and also their addition salts with a pharmaceutically acceptable acid, their addition salts with a pharmaceutically acceptable base and the enantiomers of said compounds.

The compounds according to the invention have a very good TACE-inhibiting activity and in particular they inhibit the TACE enzyme selectively relative to other ADAMs and MMPs. This inhibiting activity of the TACE enzyme is measured in an enzymatic test and quantified by the measurement of an $IC_{50}$ (inhibitory concentration necessary to obtain 50% inhibition of the TACE enzyme), as described in example 28. The compounds of the present invention have an $IC_{50}$ for TACE of less than or equal to 10 µM and more particularly of less than or equal to 1 µM. Advantageously, the compounds of the present invention have an $IC_{50}$ for TACE of less than or equal to 0.5 µM.

Advantageously, these compounds are also very selective for TACE relative to the other ADAMs and MMPs (test described in example 29): their inhibitory activity is at least ten times greater for TACE than for other ADAMs and MMPs (that is to say that the value of the $IC_{50}$ for TACE is at least ten times smaller than that for other ADAMs and MMPs), and more advantageously at least 100 times greater.

TACE (TMFα-converting enzyme) catalyses the formation of soluble TNF-α from the precursor protein (trans-membrane TNFα) bound to the membranes of certain cells. TNFα is a proinflammatory cytokine which is known for playing a role in numerous pathologies having an inflammatory nature.

The invention therefore targets the use of at least one compound of general formula (I) as defined above for the treatment of pathologies or disorders linked to a release of TNFα. An inhibitor of the TACE enzyme of general formula (I) reduces the production of TNFα. Therefore, it is of use for the treatment of pathologies linked to a release of TNFα.

The invention also targets the use of at least one compound of general formula (I) as defined above for the preparation of a pharmaceutical or cosmetic composition in which said compound has an inhibitory activity for the TACE enzyme.

Therefore it targets the use of at least one compound of general formula (I) as defined above for the treatment of pathologies or disorders which are improved by the inhibition of the TACE enzyme.

The invention also relates to a method of therapeutic (human or animal) treatment or cosmetic treatment that comprises the administration or application of a pharmaceutical or cosmetic composition comprising a compound of general formula (I) as an inhibitor of TACE and therefore as an inhibitor of the production of soluble TNFα.

Thus, the invention relates to the use of at least one compound of general formula (I) as defined above for the treatment of pathologies or disorders linked to TNFα production.

The invention also relates to the use of a compound of general formula (I) as defined above for the preparation of a medicament intended for the treatment of pathologies for which reducing the production of TNFα would be of great benefit.

Specifically, the compounds used according to the invention are particularly suitable for the treatment and prevention of disorders/diseases such as the inflammatory diseases that are listed below but that are not limiting, such as septic shock, haemodynamic shock, malaria, inflammatory bowel diseases (IBDs) such as Crohn's disease and ulcerative colitis, inflammatory bone diseases, mycobacterial infections, meningitis, fibrotic diseases, heart diseases, atherosclerosis, obesity, ischaemic attack, graft rejection, cancer, diseases involving angiogenesis phenomena, autoimmune diseases, osteoarthritis, rheumatoid arthritis, ankylosing spondylitis, chronic juvenile arthritis, multiple sclerosis, HIV, non-insulin-dependent diabetes mellitus, allergic diseases, asthma, chronic obstructive pulmonary disease (COPD), inflammatory diseases of the skin, psoriasis, atopic dermatitis and psoriatic arthritis.

These molecules are also potential active principles for the treatment of neurological pathologies having an inflammatory nature for which reducing the production of TNFα would be of great benefit. These pathologies listed below in a non-limiting manner are, for example, Alzheimer's disease, Parkinson's disease, Parkinsonian disorders, amyotrophic lateral sclerosis, autoimmune diseases of the nervous system, autonomic diseases of the nervous system, dorsal pains, cerebral oedema, cerebrovascular diseases, dementia, nerve fibre demyelinating autoimmune diseases of the nervous system, diabetic neuropathies, encephalitis, encephalomyelitis, epilepsy, chronic fatigue syndrome, giant cell arteritis, Guillain-Barré syndrome, headaches, multiple sclerosis, neuralgia, peripheral nervous system diseases, polyneuropathies, polyradiculoneuropathy, radiculopathy, respiratory paralyses, spinal cord diseases, Tourette syndrome, central nervous system vasculitis, Huntington's disease and cerebral attack.

The invention also relates to the use of a compound of general formula (I) as defined above for the preparation of a medicament intended for the treatment of pathologies having an inflammatory nature in which TNFα is involved.

The invention also relates to the use of a compound of general formula (I) as defined above for the preparation of a medicament intended for the treatment of inflammatory diseases of the skin, psoriasis, atopic dermatitis and psoriatic arthritis.

Another subject of the present invention is a pharmaceutical composition intended, in particular, for the treatment of the aforementioned afflictions, and which is characterized by the fact that it comprises, in a pharmaceutically acceptable support that is compatible with the mode of administration used for this composition, at least one compound of general formula (I). This compound of general formula (I) may also be in one of its enantiomeric forms or in the form of one of its pharmaceutically acceptable salts.

Several examples of the preparation of active compounds of formula (I) according to the invention, and also results of the biological activity of such compounds, will now be given by way of illustration and with no limiting character.

EXEMPLARY EMBODIMENTS

The compounds of general formula (I) are characterized by proton NMR analysis on an Advanced 400 MHz Bruker machine.

Example 1

4-But-2-ynyloxy-N-[2-hydroxycarbamoyl-2-(4-methanesulphonylpiperazin-1-yl)ethyl]benzamide 1-1: Dimethyl 2-(4-tert-butoxycarbonylpiperazin-1-yl)malonate 19.5 g (141 mmol) of potassium carbonate then 19.5 ml (134 mmol) of dimethyl bromomalonate are added to a solution of 25 g (134 mmol) of tert-butyl piperazine-1-carboxylate in 300 ml of acetonitrile. The reaction medium is stirred at ambient temperature for 24 h then filtered to remove the insoluble salts and concentrated under vacuum. The crude residue obtained is purified by chromatography by silica gel eluted with a 70/30 heptane/ethyl acetate mixture. 41 g (97%) of dimethyl 2-(4-tert-butoxycarbonylpiperazin-1-yl)malonate are obtained in the form of a clear oil.

1-2: Dimethyl 2-(4-tert-butoxycarbonylpiperazin-1-yl)-2-(1,3-dioxo-1,3-dihydroisoindol-2-ylmethyl) malonate 3.5 g (87 mmol) of sodium hydride are added in portions to a solution of 25 g (87 mmol) of dimethyl 2-(4-tert-butoxycarbonylpiperazin-1-yl)malonate in 250 ml of tetrahydrofuran cooled to 2° C. The reaction medium is stirred at ambient temperature for 30 minutes, then brought to 2° C. before dropwise addition of 21 g (87 mmol) of 2-(bromomethyl) isoindole-1,3-dione in 200 ml of tetrahydrofuran. The reaction medium is stirred at ambient temperature for 20 h, treated by addition of 500 ml of water then extracted with ethyl acetate. The organic phase is dried over magnesium sulphate, filtered and concentrated under vacuum.

The crude product obtained is purified by chromatography over silica gel eluted with a 70/30 heptane/ethyl acetate mixture. 27.5 g (73%) of dimethyl 2-(4-tert-butoxycarbonylpiperazin-1-yl)-2-(1,3-dioxo-1,3-dihydro-isoindol-2-ylmethyl)malonate are obtained in the form of a white solid.

1-3: Dimethyl 2-aminomethyl-2-(4-tert-butoxycarbonylpiperazin-1-yl)malonate

A solution of 2.9 ml (64 mmol) of hydrazine hydrate in 8 ml of methanol is added to a solution of 27.5 g (58 mmol) of dimethyl 2-(4-tert-butoxycarbonylpiperazin-1-yl)-2-(1,3-dioxo-1,3-dihydroisoindol-2-yl-methyl)malonate in 300 ml of methanol previously cooled to −5° C. The reaction medium is stirred from −5° C. to ambient temperature for 3 h. After evaporation and addition of 300 ml of water, the reaction medium is extracted with ethyl acetate. The organic phases are washed with a saturated aqueous solution of sodium hydrogen carbonate, dried over magnesium sulphate, filtered and evaporated. The residue obtained is purified by chromatography over silica gel eluted with an 8/2 heptane/ethyl acetate mixture then the polarity was increased to a 9/1 ethyl acetate/methanol mixture. 10 g (50%) of dimethyl 2-aminomethyl-2-(4-tert-butoxycarbonylpiperazin-1-yl)malonate are thus obtained in the form of a clear oil.

1-4: Methyl 4-but-2-ynyloxybenzoate 13.6 g (98.5 mmol) of potassium carbonate then 9.6 g (65.7 mmol) of 1-bromobut-2-yne are added to a solution containing 10 g (65.7 mmol) of methyl 4-hydroxybenzoate diluted in 250 ml of 2-butanone. The reaction medium is stirred at reflux for 5 h then at ambient temperature for 18 h. After filtration of the salts, the filtrate is concentrated under vacuum. 13.4 g (100%) of methyl 4-but-2-ynyloxybenzoate are obtained in the form of a light-yellow solid.

1-5: 4-But-2-ynyloxybenzoic acid 26 ml (262 mmol) of an aqueous solution of sodium hydroxide having a concentration of 10N are added to a solution of 13.4 g (65.7 mmol) of methyl 4-but-2-ynyloxybenzoate diluted in 200 ml of tetrahydrofuran and 25 ml of water. The reaction medium is stirred at reflux for 5 h then at 45° C. for 18 h. The reaction medium is hydrolysed, diluted with ethyl acetate then brought to pH=6 using an aqueous solution of hydrochloric acid having a concentration of 1N. The product is extracted with ethyl acetate. The organic phase is washed with water then with a saturated aqueous solution of sodium chloride, dried over magnesium sulphate, filtered and concentrated. 12.5 g (100%) of 4-but-2-ynyloxybenzoic acid are obtained in the form of a white solid.

1-6: 4-But-2-ynyloxybenzoyl chloride 2.8 ml (14.2 mmol) of dicyclohexylamine are added to a solution of 2.7 g (14.2 mmol) of 4-but-2-ynyloxybenzoic acid diluted in 30 ml of dichloromethane. After stirring for 30 min at ambient temperature, the reaction medium is cooled to 0° C. and 1.0 ml (14.2 mmol) of thionyl chloride is slowly added. The mixture is then stirred at ambient temperature for 1 h 30 min, then the dicyclohexylamine salts are precipitated by adding 50 ml of diethyl ether. After filtration of the reaction medium, the filtrate is concentrated under vacuum. 2.9 g (100%) of 4-but-2-ynyloxybenzoyl chloride are obtained in the form of a brown solid.

1-7: Dimethyl 2-(4-tert-butoxycarbonylpiperazin-1-yl)-2-[(4-but-2-ynyloxybenzoylamino)methyl]malonate 2 ml (14.2 mmol) of triethylamine then 2.9 g (14.2 mmol) of 4-but-2-ynyloxybenzoyl chloride diluted in 30 ml of tetrahydrofuran are added to a solution of 4 g (11.6 mmol) of dimethyl 2-aminomethyl-2-(4-tert-butoxycarbonylpiperazin-1-yl)malonate (prepared as described in example 1-3) in 40 ml of tetrahydrofuran. The reaction medium is stirred at ambient temperature for 1 h, then hydrolysed and the product is extracted with ethyl acetate. The organic phase is washed with water then with a saturated aqueous solution of sodium chloride, dried over magnesium sulphate, filtered and concentrated. The crude product obtained is purified by chromatography over silica gel eluted with a 5/5 heptane/ethyl acetate mixture. 4.2 g (70%) of dimethyl 2-(4-tert-butoxycarbonylpiperazin-1-yl)-2-[(4-but-2-ynyloxybenzoylamino)methyl]malonate are obtained in the form of a beige solid.

1-8: Dimethyl 2-[(4-but-2-ynyloxybenzoylamino)methyl]-2-(4-methanesulphonylpiperazin-1-yl)malonate 0.8 ml (5.7 mmol) of triethylamine then 0.4 ml (5.7 mmol) of methanesulphonyl chloride are added to a solution of 2.2 g (3.6 mmol) of dimethyl 2-(4-tert-butoxycarbonylpiperazin-1-yl)-2-[(4-but-2-ynyloxybenzoylamino)methyl]malonate in 25 ml of dichloromethane. The reaction medium is then stirred at ambient temperature for 3 h, then the solvents are evaporated under vacuum and the crude product obtained is purified by chromatography over silica gel eluted with a 98/2 dichloromethane/methanol mixture. 2 g (80%) of dimethyl 2-[(4-but-2-ynyloxybenzoylamino)methyl]-2-(4-methanesulphonylpiperazin-1-yl)malonate are obtained in the form of a white solid.

1-9: 3-(4-But-2-ynyloxybenzoylamino)-2-(4-methane-sulphonylpiperazin-1-yl)propanoic acid 0.5 ml (0.5 mmol) of an aqueous solution of sodium hydroxide having a concentration of 1N are added to a solution of 100 mg (0.2 mmol) of dimethyl 2-[(4-but-2-ynyloxybenzoylamino)methyl]-2-(4-methanesulphonylpiperazin-1-yl)malonate in 4 ml of tetrahydrofuran and 1 ml of methanol. The reaction medium is stirred at ambient temperature for 48 h then hydrolysed, diluted with ethyl acetate and brought to pH=6 with an aqueous solution of hydrochloric acid having a concentration of 1N. After extraction with ethyl acetate, the organic phase is washed with water then with a saturated aqueous solution of sodium chloride. After drying over magnesium sulphate and filtering, the solvent is concentrated under vacuum. The crude product obtained is purified by recrystallization in ethyl acetate. 30 mg (32%) of 3-(4-but-2-ynyloxybenzoylamino)-2-(4-methanesulphonylpiperazin-1-yl)propanoic acid are obtained in the form of a white solid.

1-10: N-[2-tert-butoxycarbamoyl-2-(4-methane-sulphonylpiperazin-1-yl)ethyl]-4-but-2-ynyloxybenzamide 50 mg (0.4 mmol) of 1-hydroxybenzotriazole then 70 mg (0.4 mmol) of 1-ethyl-3-(3-dimethylamino-propyl)carbodiimide hydrochloride are added to a solution of 100 mg (0.2 mmol) of 3-(4-but-2-ynyloxybenzoylamino)-2-(4-methanesulphonylpiperazin-1-yl)propanoic acid in 2 ml of dichloromethane and 2 ml of dimethylformamide. The reaction medium is stirred for 20 min before adding a mixture containing 30 mg (0.3 mmol) of O-tert-butylhydroxylamine hydrochloride and 40 µl (0.3 mmol) of triethylamine. The mixture is then stirred at ambient temperature for 20 h. Dichloromethane is added, the organic phase is washed with a saturated aqueous solution of sodium hydrogen carbonate then with water, dried over magnesium sulphate, filtered and concentrated under vacuum. 100 mg (85%) of N-[2-tert-butoxycarbamoyl-2-(4-methanesulphonylpiperazin-1-yl)ethyl]-4-but-2-ynyloxy benzamide are obtained in the form of a white solid.

1-11: 4-But-2-ynyloxy-N-[2-hydroxycarbamoyl-2-(4-methanesulphonylpiperazin-1-yl)ethyl]benzamide 100 mg (0.2 mmol) of N-[2-tert-butoxycarbamoyl-2-(4-methanesulphonylpiperazin-1-yl)ethyl]-4-but-2-ynyloxybenzamide are placed in 3 ml of trifluoroacetic acid. After stirring for 8 days at ambient temperature, the mixture is concentrated under vacuum then the crude product is purified by chromatography over silica gel eluted with a 9/1 dichloromethane/methanol mixture. 30 mg (34%) of 4-but-2-ynyloxy-N-[2-hydroxycarbamoyl-2-(4-methanesulphonylpiperazin-1-yl)ethyl]benzamide are obtained in the form of a beige solid.

$^1$H NMR (δ, DMSO): 1.90 (s, 3H); 2.71-2.75 (m, 4H); 2.91 (s, 3H); 3.10-3.14 (m, 4H); 3.55 (m, 2H); 3.60 (m, 1H); 4.86 (s, 2H); 7.07 (d, J=8.9 Hz, 2H); 7.50 (m, 1H); 7.86 (d, J=8.9 Hz, 2H); 8.38 (s, 1H); 8.95 (s, 1H).

Example 2

4-But-2-ynyloxy-N—[(S)-2-hydroxycarbamoyl-2-(4-methanesulphonylpiperazin-1-yl)ethyl]benzamide 2-1: N,N-bis(2-chloroethyl)methanesulphonamide 8.6 ml (62 mmol) of triethylamine are added to a solution of 5 g (28 mmol) of bis(2-chloroethyl)amine hydrochloride in 60 ml of dichloromethane. After filtration of the salts, 2.4 ml (31 mmol) of methanesulphonyl chloride are added to the filtrate obtained and the reaction medium is stirred at ambient temperature for 3 h. After addition of water, the product is extracted with dichloromethane. The organic phase is washed with water, dried over magnesium sulphate, filtered and concentrated. 5.8 g (94%) of N,N-bis(2-chloroethyl)methanesulphonamide are obtained in the form of a beige solid.

2-2: Methyl (S)-3-tert-butoxycarbonylamino-2-(4-methanesulphonylpiperazin-1-yl)propanoate A solution of 5 g (20 mmol) of methyl (S)-2-amino-3-tert-butoxycarbonylaminopropanoate hydrochloride and 4.3 g (20 mmol) of N,N-bis(2-chloroethyl)methanesulphonamide in 65 ml of N,N-diisopropylethylamine is heated at 127° C. with vigorous stirring for 18 h. After addition of water, the product is extracted with ethyl acetate. The organic phases are combined, washed with water, dried over magnesium sulphate, filtered and concentrated under vacuum. The crude product obtained is purified by chromatography over silica gel eluted with a 50/50 heptane/ethyl acetate mixture. 3.3 g (46%) of methyl (S)-3-tert-butoxycarbonylamino-2-(4-methanesulphonylpiperazin-1-yl)propanoate are obtained in the form of a white solid.

2-3: Methyl (S)-3-amino-2-(4-methanesulphonylpiperazin-1-yl)propanoate hydrochloride 15 ml of a solution of hydrochloric acid in isopropanol having a concentration of 5-6N are added dropwise to a solution of 2.7 g (7.4 mmol) of methyl (S)-3-tert-butoxycarbonylamino-2-(4-methanesulphonylpiperazin-1-yl)propanoate in 30 ml of methanol. The reaction medium is stirred at 40° C. for 2 h, concentrated under vacuum then taken up in 20 ml of methanol and 150 ml of diethyl ether. The product precipitates, is filtered, rinsed with diethyl ether then dried under vacuum. 2.3 g (100%) of methyl (S)-3-amino-2-(4-methanesulphonylpiperazin-1-yl)propanoate hydrochloride are obtained in the form of a white solid.

2-4: Methyl (S)-3-(4-but-2-ynyloxybenzoylamino)-2-(4-methanesulphonylpiperazin-1-yl)propanoate 210 mg (1.5 mmol) of 1-hydroxybenzotriazole and 290 mg (1.5 mmol) of 1-ethyl-3-(3-dimethylamino-propyl)carbodiimide hydrochloride are added to a solution of 260 mg (1.9 mmol) of 4-but-2-ynyloxybenzoic acid (prepared as described in example 1-5) in 10 ml of dimethylformamide. The reaction medium is stirred for 15 minutes and a mixture of 420 mg (1.4 mmol) of methyl (S)-3-amino-2-(4-methanesulphonylpiperazin-1-yl)propanoate hydrochloride and 390 mg (2.8 mmol) of triethylamine in 3 ml of dimethylformamide are added. The reaction medium is stirred at ambient temperature for 1 h 30 min, heated to 50° C., over 1 h 30 min then hydrolysed with a saturated aqueous solution of sodium hydrogen carbonate and extracted with ethyl acetate. The organic phase is washed with an aqueous solution of sodium hydrogen carbonate then with a saturated aqueous solution of sodium chloride, dried over magnesium sulphate, filtered and concentrated. The crude product obtained is purified by chromatography over silica gel eluted with a 98/2 dichloromethane/methanol mixture. 620 mg (100%) of methyl (S)-3-(4-but-2-ynyloxybenzoylamino)-2-(4-methanesulphonylpiperazin-1-yl)propanoate are obtained in the form of a colourless oil.

2-5: (S)-3-(4-but-2-ynyloxybenzoylamino)-2-(4-methane-sulphonylpiperazin-1-yl)propanoic acid 2.1 ml (2.1 mmol) of an aqueous solution of lithium hydroxide having a concentration of 1N are added to a solution of 610 mg (1.4 mmol) of methyl (S)-3-(4-but-2-ynyloxybenzoylamino)-2-(4-methanesulphonylpiperazin-1-yl)propanoate in 12 ml of tetrahydrofuran and 2 ml of water. The reaction medium is stirred at ambient temperature for 18 h then the solvents are concentrated under vacuum. The mixture is brought to pH=6 by addition of 2.5 ml of an aqueous solution of hydrochloric acid having a concentration of 1N. The solid which precipitates is filtered, rinsed with water then with diethyl ether, and dried under vacuum. 420 mg (72%) of (S)-3-(4-but-2-ynyloxybenzoylamino)-2-(4-methanesulphonylpiperazin-1-yl)propanoic acid are obtained in the form of a white solid.

2-6: 4-But-2-ynyloxy-N—[(S)-2-hydroxycarbamoyl-2-(4-methanesulphonylpiperazin-1-yl)ethyl]benzamide 150 mg (1.1 mmol) of 1-hydroxybenzotriazole and 210 mg (1.1 mmol) of 1-ethyl-3-(3-dimethylamino-propyl)carbodiimide hydrochloride are added to a solution of 420 mg (1 mmol) of (S)-3-(4-but-2-ynyloxybenzoylamino)-2-(4-methanesulphonylpiperazin-1-yl)propanoic acid in 8 ml of dimethylformamide. The reaction medium is stirred for 20 minutes then 160 mg (1.1 mmol) of O-tert-butyldimethylsilylhydroxylamine in 2 ml of dimethylformamide are added. The mixture is then stirred at ambient temperature for 24 h then hydrolysed with 10 ml of a 5% aqueous citric acid solution and stirred for a further 1 h. By adding a saturated aqueous solution of sodium hydrogen carbonate, the pH is brought to 8 and the product extracted with 2-butanol.

The organic phase is washed with water then with a saturated aqueous solution of sodium chloride and concentrated. The crude product obtained is recrystallized in ethanol and 320 mg (74%) of 4-but-2-ynyloxy-N—[(S)-2-hydroxycarbamoyl-2-(4-methane-sulphonylpiperazin-1-yl)ethyl]benzamide are obtained in the form of a white solid having a melting point of 127° C.

$^1$H NMR (δ, DMSO): 1.84 (s, 3H); 2.60-2.70 (m, 4H); 2.84 (s, 3H); 2.95-3.10 (m, 4H); 3.40-3.50 (m, 2H); 3.51-3.58 (m, 1H); 4.81 (s, 2H); 7.03 (d, J=7.2 Hz, 2H); 7.80 (d, J=7.2 Hz, 2H); 8.64 (s, 1H).

Example 3

4-But-2-ynyloxy-N—[(R)-2-hydroxycarbamoyl-2-(4-methanesulphonylpiperazin-1-yl)ethyl]benzamide 3-1: N,N-bis(2-chloroethyl)methanesulphonamide 17 ml (123.2 mmol) of triethylamine are added to a solution of 10 g (56 mmol) of bis(2-chloroethyl)amine hydrochloride in 100 ml of dichloromethane. After filtration of the salts, 4.6 ml (58.8 mmol) of methanesulphonyl chloride are added to the filtrate obtained and the reaction medium is stirred at ambient temperature for 3 h. After addition of water, the product is extracted with dichloromethane. The organic phase is washed with water, dried over magnesium sulphate, filtered and concentrated. 11.6 g (94%) of N,N-bis(2-chloroethyl) methanesulphonamide are obtained in the form of a beige solid.

3-2: Methyl (R)-3-tert-butoxycarbonylamino-2-(4-methanesulphonylpiperazin-1-yl)propanoate A solution of 6 g (23.6 mmol) of methyl (R)-2-amino-3-tert-butoxycarbonylaminopropanoate hydrochloride and 5.2 g (23.6 mmol) of N,N-bis(2-chloroethyl)methanesulphonamide in 80 ml of N,N-diisopropylethylamine is heated at 125° C. with vigorous stirring for 18 h. After addition of water, the product is extracted with ethyl acetate. The organic phases are combined, washed with water, dried over magnesium sulphate, filtered and concentrated under vacuum. The crude product obtained is purified by chromatography over silica gel eluted with a 5/5 heptane/ethyl acetate mixture. 3.8 g (44%) of methyl (R)-3-tert-butoxycarbonylamino-2-(4-methanesulphonylpiperazin-1-yl)propanoate are obtained in the form of a white solid.

3-3: Methyl (R)-3-amino-2-(4-methanesulphonylpiperazin-1-yl)propanoate hydrochloride 15 ml of a solution of hydrochloric acid in isopropanol having a concentration of 5-6N are added dropwise to a solution of 3.8 g (10.4 mmol) of methyl (R)-3-tert-butoxycarbonylamino-2-(4-methanesulphonylpiperazin-1-yl)propanoate in 50 ml of methanol. The reaction medium is stirred at 40° C. for 3 h, concentrated under vacuum then taken up in diethyl ether. The product precipitates, is filtered, rinsed with diethyl ether then dried under vacuum. 3 g (97%) of methyl (R)-3-amino-2-(4-methanesulphonylpiperazin-1-yl)propanoate hydrochloride are obtained in the form of a beige solid.

3-4: Methyl (R)-3-(4-but-2-ynyloxybenzoylamino)-2-(4-methanesulphonylpiperazin-1-yl)propanoate In a manner similar to example 2-4, starting from 0.5 g (3.3 mmol) of 4-but-2-ynyloxybenzoic acid (prepared as described in example 1-5) and 1 g (3.3 mmol) of methyl (R)-3-amino-2-(4-methanesulphonylpiperazin-1-yl)propanoate hydrochloride, 1.3 g (90%) of methyl (R)-3-(4-but-2-ynyloxybenzoylamino)-2-(4-methanesulphonylpiperazin-1-yl)propanoate are obtained in the form of a white solid.

3-5: (R)-3-(4-but-2-ynyloxybenzoylamino)-2-(4-methane-sulphonylpiperazin-1-yl)propanoic acid In a manner similar to example 2-5, starting from 1.3 g (3 mmol) of methyl (R)-3-(4-but-2-ynyloxybenzoylamino)-2-(4-methanesulphonylpiperazin-1-yl)propanoate, 950 mg (75%) of (R)-3-(4-but-2-ynyloxybenzoylamino)-2-(4-methanesulphonylpiperazin-1-yl)propanoic acid are obtained in the form of a white solid.

3-6: 4-But-2-ynyloxy-N—[(R)-2-hydroxycarbamoyl-2-(4-methanesulphonylpiperazin-1-yl)ethyl]benzamide In a manner similar to example 2-6, starting from 950 mg of (R)-3-(4-but-2-ynyloxybenzoylamino)-2-(4-methanesulphonylpiperazin-1-yl)propanoic acid, 60 mg (60%) of 4-but-2-ynyloxy-N—[(R)-2-hydroxycarbamoyl-2-(4-methanesulphonylpiperazin-1-yl)ethyl]benzamide are obtained in the form of a white solid having a melting point of 211° C.

HPLC/MS analysis: C18 Gemini column, 150×3 mm, 3 microns, flow rate: 0.5 ml/min, acetonitrile+0.1% formic acid/water+0.1% formic acid Retention time: 9.5 min, M+H: 439.

Example 4

N—[(S)-2-hydroxycarbamoyl-2-(4-methane-sulphonylpiperazin-1-yl)ethyl]-4-methoxybenzamide 4-1: Methyl 4-(2-methoxyethoxymethoxy)benzoate 3.2 g (78.9 mmol) of 60% sodium hydride are added to a solution of 10 g (65.7 mmol) of methyl 4-hydroxybenzoate in 50 ml of tetrahydrofuran and 50 ml of dimethylformamide. The reaction medium is stirred at ambient temperature for 20 minutes then 8.3 g (72.3 mmol) of 2-methoxyethoxymethyl chloride are added. After stirring for 24 h at ambient temperature, the mixture is poured over water then extracted with ethyl acetate. The organic phase is washed with water then with a saturated aqueous solution of sodium chloride, dried over magnesium sulphate, filtered and concentrated. 16 g (100%) of methyl 4-(2-methoxyethoxymethoxy)benzoate are obtained in the form of a colourless oil.

4-2: 4-(2-Methoxyethoxymethoxy)benzoic acid 15 g (375 mmol) of sodium hydroxide powder are added to a solution of 18 g (75 mmol) of methyl 4-(2-methoxyethoxymethoxy)benzoate in 250 ml of tetrahydrofuran, 80 ml of water and 30 ml of methanol. The reaction medium is stirred at 40° C. for 18 h then hydrolysed, diluted with ethyl acetate and brought to pH=6 with an aqueous solution of hydrochloric acid having a concentration of 1N. After extracting with ethyl acetate, the organic phase is washed with water then with a saturated aqueous solution of sodium chloride, dried over magnesium sulphate, filtered then concentrated. 16 g (95%) of 4-(2-methoxyethoxy-methoxy)benzoic acid are obtained in the form of a white solid.

4-3: Methyl (S)-2-(4-methanesulphonylpiperazin-1-yl)-3-[4-(2-methoxyethoxymethoxy)benzoylamino]propanoate 1.1 g (5 mmol) of 4-(2-methoxyethoxymethoxy)benzoic acid are put into solution in 15 ml of dimethylformamide then 0.7 g (5.5 mmol) of 1-hydroxybenzotriazole and 1.1 g (5.5 mmol) of 1-ethyl-3-(3-dimethylaminopropyl)carbodiimide hydrochloride are added. The reaction medium is stirred for 20 minutes before adding a mixture of 1.5 g (5 mmol) of methyl (S)-3-amino-2-(4-methanesulphonylpiperazin-1-yl)propanoate hydrochloride (prepared as described in 2-3) and of 1.4 ml (9.9 mmol) of triethylamine in 15 ml of dimethylformamide. The reaction medium is stirred at 50° C. for 1 h 30 min then at ambient temperature for 18 h. After hydrolysis with a saturated aqueous solution of sodium hydrogen carbonate then extraction with ethyl acetate, the organic phase is washed with an aqueous solution of sodium hydrogen carbonate then with a saturated aqueous solution of sodium chloride, dried over magnesium sulphate, filtered and concentrated. The crude product obtained is purified by chromatography over silica gel eluted with a 9/1 dichloromethane/methanol mixture. 1.6 g (68%) of methyl (S)-2-(4-methanesulphonylpiperazin-1-yl)-3-[4-(2-methoxyethoxymethoxy)benzoylamino]propanoate are obtained in the form of a colourless oil.

4-4: Methyl (S)-3-(4-hydroxybenzoylamino)-2-(4-methanesulphonylpiperazin-1-yl)propanoate 0.5 ml of 98% sulphuric acid are added to a solution of 1.6 g (3.4 mmol) of methyl (S)-2-(4-methanesulphonylpiperazin-1-yl)-3-[4-(2-methoxyethoxymethoxy)benzoyl-amino]propanoate in 15 ml of tetrahydrofuran and 15 ml of methanol. After stirring for 18 h at ambient temperature, the reaction medium is hydrolysed with a saturated aqueous solution of sodium hydrogen carbonate then extracted with ethyl acetate. The organic phase is washed with water then with a saturated aqueous solution of sodium chloride, dried over magnesium sulphate, filtered and concentrated. 1.1 g (85%) of methyl (S)-3-(4-hydroxybenzoylamino)-2-(4-methanesulphonylpiperazin-1-yl)propanoate are obtained in the form of a white solid.

4-5: Methyl (S)-2-(4-methanesulphonylpiperazin-1-yl)-3-(4-methoxybenzoylamino)propanoate 100 mg (0.8 mmol) of potassium carbonate and 0.1 ml (2 mmol) of methyl iodide are added to a solution of 250 mg (0.7 mmol) of methyl (S)-3-(4-hydroxybenzoylamino)-2-(4-methanesulphonylpiperazin-1-yl)propanoate in 10 ml of methyl ethyl ketone. The reaction medium is heated at 80° C. for 4 h. After cooling, it is filtered then concentrated. 260 mg (100%) of methyl (S)-2-(4-methanesulphonylpiperazin-1-yl)-3-(4-methoxybenzoylamino)-propanoate are obtained in the form of a white solid.

4-6: (S)-2-(4-Methanesulphonylpiperazin-1-yl)-3-(4-methoxybenzoylamino)propanoic acid 1 ml (1 mmol) of an aqueous solution of lithium hydroxide having a concentration of 1N is added to a solution of 260 mg (0.7 mmol) of methyl (S)-2-(4-methanesulphonylpiperazin-1-yl)-3-(4-methoxybenzoyl-amino)propanoate in 8 ml of tetrahydrofuran and 1 ml of water. The reaction medium is stirred at ambient temperature for 20 h. The solvents are concentrated under vacuum, the reaction medium is brought to pH=6 with an aqueous solution of acetic acid having a concentration of 1N. The product precipitates and the residue is taken up in 10 ml of water and stirred for 1 h. The solid is filtered, rinsed with water and with diethyl ether then dried. 190 mg (76%) of (S)-2-(4-methanesulphonylpiperazin-1-yl)-3-(4-methoxybenzoyl-amino)propanoic acid are obtained in the form of a white solid.

4-7: N—[(S)-2-Hydroxycarbamoyl-2-(4-methane-sulphonylpiperazin-1-yl)ethyl]-4-methoxybenzamide In a manner similar to example 2-6, starting from 200 mg (0.5 mmol) of (S)-2-(4-methanesulphonylpiperazin-1-yl)-3-(4-methoxybenzoyl-amino)propanoic acid, 60 mg (31%) of N—[(S)-2-hydroxycarbamoyl-2-(4-methanesulphonylpiperazin-1-yl)ethyl]-4-methoxybenzamide are obtained in the form of a beige solid having a melting point of 158° C.

$^1$H NMR (δ, DMSO): 2.70-2.77 (m, 4H); 2.85 (s, 3H); 3.02-3.15 (m, 4H); 3.30 (s, 1H); 3.45 (m, 1H); 3.60 (m, 1H); 3.82 (s, 3H); 7.02 (d, J=8.4 Hz, 2H); 7.85 (d, J=8.4 Hz, 2H); 8.35 (s, 1H); 8.94 (s, 1H); 10.67 (s, 1H).

Example 5

4-cyclopropylmethoxy-N—[(S)-2-hydroxycarbamoyl-2-(4-methanesulphonylpiperazin-1-yl)ethyl]benzamide

5-1: Methyl (S)-3-(4-cyclopropylmethoxybenzoylamino)-2-(4-methanesulphonylpiperazin-1-yl)propanoate In a manner similar to example 4-5, starting from 250 mg (0.7 mmol) of methyl (S)-3-(4-hydroxybenzoylamino)-2-(4-methanesulphonylpiperazin-1-yl)propanoate (prepared as described in example 4-4) and from 0.5 ml (5.2 mmol) of (bromoethyl)cyclopropane, 290 mg (100%) of methyl (S)-3-(4-cyclopropylmethoxybenzoylamino)-2-(4-methane-sulphonylpiperazin-1-yl)propanoate are obtained in the form of a white solid.

5-2: (S)-3-(4-Cyclopropylmethoxybenzoylamino)-2-(4-methanesulphonylpiperazin-1-yl)propanoic acid In a manner similar to example 2-5, starting from 290 mg (0.7 mmol) of methyl (S)-3-(4-cyclopropylmethoxybenzoylamino)-2-(4-methanesulphonylpiperazin-1-yl)propanoate, 240 mg (86%) of (S)-3-(4-cyclopropylmethoxybenzoylamino)-2-(4-methanesulphonylpiperazin-1-yl)propanoic acid are obtained in the form of a white solid.

5-3: 4-Cyclopropylmethoxy-N—[(S)-2-hydroxycarbamoyl-2-(4-methanesulphonylpiperazin-1-yl)ethyl]benzamide In a manner similar to example 2-6, starting from 240 mg (0.6 mmol) of (S)-3-(4-cyclopropylmethoxybenzoylamino)-

2-(4-methanesulphonylpiperazin-1-yl)propanoic acid, 10 mg (4%) of 4-cyclopropylmethoxy-N—[(S)-2-hydroxycarbamoyl-2-(4-methanesulphonylpiperazin-1-yl)ethyl]benzamide are obtained in the form of a beige solid.

HPLC/MS analysis: C18 Gemini column, 150×3 mm, 3 microns, flow rate: 0.5 ml/min, acetonitrile+0.1% formic acid/water+0.1% formic acid Retention time: 21 min, M+H: 441.

Example 6

4-benzyloxy-N—[(S)-2-hydroxycarbamoyl-2-(4-methanesulphonylpiperazin-1-yl)ethyl]benzamide 6-1: Methyl (S)-3-(4-benzyloxybenzoylamino)-2-(4-methanesulphonylpiperazin-1-yl)propanoate In a manner similar to example 4-5, starting from 300 mg (0.8 mmol) of methyl (S)-3-(4-hydroxybenzoylamino)-2-(4-methanesulphonylpiperazin-1-yl)propanoate (prepared as described in example 4-4) and from 0.1 ml (0.9 mmol) of benzyl bromide, 370 mg (100%) of methyl (S)-3-(4-benzyloxybenzoylamino)-2-(4-methanesulphonylpiperazin-1-yl)propanoate are obtained in the form of a white solid.

6-2: (S)-3-(4-Benzyloxybenzoylamino)-2-(4-methane-sulphonylpiperazin-1-yl)propanoic acid In a manner similar to example 2-5, starting from 370 mg (0.8 mmol) of methyl (S)-3-(4-benzyloxybenzoylamino)-2-(4-methanesulphonylpiperazin-1-yl)propanoate, 340 mg (94%) of (S)-3-(4-benzyloxybenzoylamino)-2-(4-methane-sulphonylpiperazin-1-yl)propanoic acid are obtained in the form of a white solid.

6-3: 4-Benzyloxy-N—[(S)-2-hydroxycarbamoyl-2-(4-methanesulphonylpiperazin-1-yl)ethyl]benzamide In a manner similar to example 2-6, starting from 340 mg (0.7 mmol) of (S)-3-(4-benzyloxybenzoylamino)-2-(4-methanesulphonylpiperazin-1-yl)propanoic acid, 160 mg (46%) of 4-benzyloxy-N—[(S)-2-hydroxycarbamoyl-2-(4-methanesulphonylpiperazin-1-yl)ethyl]benzamide are obtained in the form of a beige solid having a melting point of 150° C.

$^1$H NMR (δ, DMSO): 2.65-2.80 (m, 4H); 2.88 (s, 3H); 3.04-3.15 (m, 4H); 3.35 (m, 1H); 3.40-3.50 (m, 1H); 3.57-3.63 (m, 1H); 5.21 (s, 2H); 7.11 (d, J=8.6 Hz, 2H); 7.31-7.45 (m, 3H); 7.45-7.51 (m, 2H); 7.85 (d, J=8.6 Hz, 2H); 8.36 (s, 1H); 8.94 (s, 1H); 10.67 (s, 1H).

Example 7

4-butoxy-N—[(S)-2-hydroxycarbamoyl-2-(4-methanesulphonylpiperazin-1-yl)ethyl]benzamide 7-1: Methyl (S)-3-(4-butoxybenzoylamino)-2-(4-methane-sulphonylpiperazin-1-yl)propanoate In a manner similar to example 4-5, starting from 250 mg (0.7 mmol) of methyl (S)-3-(4-hydroxybenzoylamino)-2-(4-methanesulphonylpiperazin-1-yl)propanoate (prepared as described in example 4-4) and from 0.5 ml (5 mmol) of butyl iodide, 300 mg (100%) of methyl (S)-3-(4-butoxybenzoylamino)-2-(4-methanesulphonylpiperazin-1-yl)propanoate are obtained in the form of a white solid.

7-2: (S)-3-(4-Butoxybenzoylamino)-2-(4-methane-sulphonylpiperazin-1-yl)propanoic acid In a manner similar to example 2-5, starting from 300 mg (0.7 mmol) of methyl (S)-3-(4-butoxybenzoylamino)-2-(4-methanesulphonylpiperazin-1-yl)propanoate, 200 mg (71%) of (S)-3-(4-butoxybenzoylamino)-2-(4-methanesulphonylpiperazin-1-yl)propanoic acid are obtained in the form of a white solid.

7-3: 4-Butoxy-N—[(S)-2-hydroxycarbamoyl-2-(4-methane-sulphonylpiperazin-1-yl)ethyl]benzamide In a manner similar to example 2-6, starting from 200 mg (0.5 mmol) of (S)-3-(4-butoxybenzoylamino)-2-(4-methane-sulphonylpiperazin-1-yl)propanoic acid, 100 mg (55%) of 4-butoxy-N—[(S)-2-hydroxycarbamoyl-2-(4-methane-sulphonylpiperazin-1-yl)ethyl]benzamide are obtained in the form of a beige solid having a melting point of 130° C.

$^1$H NMR (δ, DMSO): 0.95 (t, J=7.4 Hz, 3H); 1.40-1.49 (m, 2H); 1.68-1.75 (m, 2H); 2.60-2.75 (m, 4H); 2.86 (s, 3H); 3.03-3.11 (m, 4H); 3.32 (m, 1H); 3.40-3.45 (m, 1H); 3.52-3.60 (m, 1H); 4.04 (t, J=7.6 Hz, 2H); 7.00 (d, J=8.8 Hz, 2H); 7.85 (d, J=8.9 Hz, 2H); 8.31 (t, J=5 Hz, 1H); 8.91 (s, 1H); 10.63 (s, 1H).

Example 8

4-but-2-ynyloxy-N-{(S)-2-hydroxycarbamoyl-2-[4-(toluene-4-sulphonyl)piperazin-1-yl]ethyl}benzamide 8-1: Ethyl 2-[(toluene-4-sulphonyl)(2-trifluoromethane-sulphonyloxyethyl)amino]trifluoromethanesulphonate 7.1 ml (42.5 mmol) of trifluoromethanesulphonic anhydride are added dropwise to a solution of 5 g (19.3 mmol) of N,N-bis(2-chloroethyl)-4-methylbenzene-sulphonamide and 3.4 ml (42.5 mmol) of pyridine in 75 ml of dichloromethane. The reaction medium is stirred at ambient temperature for 18 h. After addition of water, it is extracted with dichloromethane. 9 g of crude residue are obtained and purified by chromatography over silica gel eluted with an 8/2 heptane/ethyl acetate mixture. 5 g (50%) of ethyl 2-[(toluene-4-sulphonyl)(2-trifluoromethanesulphonyl-oxyethyl)amino]trifluoromethanesulphonate are obtained in the form of a white solid.

8-2: Methyl (S)-3-tert-butoxycarbonylamino-2-[4-(toluene-4-sulphonyl)piperazin-1-yl]propanoate A solution of 2 g (3.9 mmol) of ethyl 2-[(toluene-4-sulphonyl)(2-trifluoromethanesulphonyloxyethyl)amino]-trifluoromethanesulphonate, 1 g (3.9 mmol) of methyl 2-amino-3-tert-butoxypropanoate hydrochloride and 1.8 g (12.9 mmol) of potassium carbonate in 25 ml of acetonitrile is heated at 60° C. for 18 h. After addition of water, the medium is extracted with ethyl acetate. The organic phase is dried over magnesium sulphate, filtered and evaporated. 3 g of crude residue are obtained and purified by chromatography over silica gel eluted with an 8/2 heptane/ethyl acetate mixture then the polarity was increased to 7/3. 1 g (60%) of methyl (S)-3-tert-butoxycarbonylamino-2-[4-(toluene-4-sulphonyl)piperazin-1-yl]propanoate are obtained in the form of a white solid.

8-3: Methyl (S)-3-amino-2-[4-(toluene-4-sulphonyl)piperazin-1-yl]propanoate

A solution containing 1 g (2.3 mmol) of methyl (S)-3-tert-butoxycarbonylamino-2-[4-(toluene-4-sulphonyl)piperazin- 1-yl]propanoate in 10 ml of dichloromethane and 2.6 ml (3.4 mmol) of trifluoroacetic acid is stirred at ambient temperature for 18 h. After addition of a saturated aqueous solution of sodium hydrogen carbonate up to a pH of 8, the reaction medium is extracted with dichloromethane. The organic phase is dried over magnesium sulphate, filtered and evaporated. 780 mg (100%) of methyl (S)-3-amino-2-[4-(toluene-4-sulphonyl)piperazin-1-yl]propanoate are obtained in the form of an oil.

8-4: Methyl (S)-3-(4-but-2-ynyloxybenzoylamino)-2-[4-(toluene-4-sulphonyl)piperazin-1-yl]propanoate 700 mg (2.1 mmol) of methyl (S)-3-amino-2-[4-(toluene-4-sulphonyl)piperazin-1-yl]propanoate in 3 ml of dimethylformamide are added to a solution containing 390 mg (2.1 mmol) of 4-but-2-ynyloxybenzoic acid (prepared as described in example 1-5), 304 mg (2.3 mmol) of 1-hydroxybenzotriazole, and 431 mg (2.3 mmol) of 1-ethyl-3-(3-dimethylaminopropyl)carbodiimide hydrochloride in 5 ml of DMF. The reaction medium is stirred for 17 h at ambient temperature. After addition of ethyl acetate and water, the reaction medium is brought to a pH of 8 with an aqueous solution of sodium hydrogen carbonate and extracted with ethyl acetate. The organic phase is washed with water, dried over magnesium sulphate, filtered, and evaporated.
The crude product obtained is purified by chromatography over silica gel eluted with an 8/2 heptane/ethyl acetate mixture then the polarity was increased to 4/6. 1 g (95%) of methyl (S)-3-(4-but-2-ynyloxybenzoylamino)-2-[4-(toluene-4-sulphonyl)-piperazin-1-yl]propanoate is obtained in the form of a white solid.

8-5: (S)-3-(4-But-2-ynyloxybenzoylamino)-2-[4-(toluene-4-sulphonyl)piperazin-1-yl]propanoic acid 1.6 ml (1.6 mmol) of a 1M aqueous solution of lithium hydroxide are added to a solution of 400 mg (0.8 mmol) of methyl (S)-3-(4-but-2-ynyloxybenzoylamino)-2-[4-(toluene-4-sulphonyl)piperazin-1-yl]propanoate in 5 ml of tetrahydrofuran and the medium is stirred at ambient temperature for 20 h. After addition of water and of acetic acid up to a pH of 4, the reaction medium is extracted with ethyl acetate. The organic phase is dried over sodium sulphate then filtered and concentrated under vacuum. 400 mg (100%) of (S)-3-(4-but-2-ynyloxybenzoylamino)-2-[4-(toluene-4-sulphonyl) piperazin-1-yl]propanoic acid are obtained in the form of a white solid.

8-6: 4-But-2-ynyloxy-N-{(S)-2-hydroxycarbamoyl-2-[4-(toluene-4-sulphonyl)piperazin-1-yl] ethyl}benzamide In a manner similar to example 2-6, starting from 400 mg (0.8 mmol) of (S)-3-(4-but-2-ynyloxybenzoylamino)-2-[4-(toluene-4-sulphonyl)piperazin-1-yl]-propanoic acid, and after purification by chromatography over silica gel eluted with a 98/2 dichloromethane/methanol mixture, 150 mg (37%) of 4-but-2-ynyloxy-N-{(S)-2-hydroxycarbamoyl-2-[4-(toluene-4-sulphonyl)piperazin-1-yl]ethyl}benzamide are obtained in the form of a white solid.
$^1$H NMR (δ, DMSO): 1.90 (s, 3H); 2.47 (s, 3H); 2.65 (m, 2H); 2.75 (m, 2H); 2.85 (m, 4H); 3.25-3.40 (m, 2H); 3.55 (m, 1H); 4.85 (s, 2H); 7.02 (d, J=8.8 Hz, 2H); 7.52 (m, 2H); 7.66 (m, 2H); 7.77 (d, J=8 Hz, 2H); 8.29 (t, J=5.6 Hz, 1H); 8.90 (s, 1H); 10.63 (s, 1H).

Example 9

4-(4-fluorobenzyloxy)-N—[(S)-2-hydroxycarbamoyl-2-(4-methanesulphonylpiperazin-1-yl)ethyl]benzamide 9-1: Methyl (S)-3-[4-(4-fluorobenzyloxy)benzoylamino]-2-(4-methanesulphonylpiperazin-1-yl)propanoate In a manner similar to example 4-5, starting from 170 mg (0.8 mmol) of methyl (S)-3-(4-hydroxybenzoylamino)-2-(4-methanesulphonylpiperazin-1-yl)propanoate (prepared as described in example 4-4) and from 0.1 ml (0.7 mmol) of 1-bromomethyl-4-fluorobenzene, 220 mg (100%) of methyl (S)-3-[4-(4-fluorobenzyloxy)benzoyl-amino]-2-(4-methanesulphonylpiperazin-1-yl)propanoate are obtained in the form of a white solid.

9-2: (S)-2-(4-Methanesulphonylpiperazin-1-yl)-3-[4-(4-fluorobenzyloxy)benzoylamino]propanoic acid In a manner similar to example 2-5, starting from 220 mg (0.4 mmol) of methyl (S)-3-[4-(4-fluorobenzyl-oxy)benzoylamino]-2-(4-methanesulphonylpiperazin-1-yl)-propanoate, 180 mg (86%) of (S)-2-(4-methane-sulphonylpiperazin-1-yl)-3-[4-(4-fluorobenzyloxy)-benzoylamino]propanoic acid are obtained in the form of a white solid.

9-3: 4-(4-Fluorobenzyloxy)-N—[(S)-2-hydroxycarbamoyl-2-(4-methanesulphonylpiperazin-1-yl)ethyl] benzamide In a manner similar to example 2-6, starting from 180 mg (0.4 mmol) of (S)-2-(4-methanesulphonylpiperazin-1-yl)-3-[4-(4-fluorobenzyloxy)benzoylamino]propanoic acid, 130 mg (65%) of 4-(4-fluorobenzyloxy)-N—[(S)-2-hydroxycarbamoyl-2-(4-methanesulphonylpiperazin-1-yl)-ethyl]benzamide are obtained in the form of a white solid having a melting point of 194° C.
$^1$H NMR (δ, DMSO): 3.00 (s, 3H); 3.10-3.50 (m, 8H); 3.60-3.70 (m, 1H); 3.72-3.90 (m, 2H); 5.16 (s, 2H); 7.08 (d, J=8.8 Hz, 2H); 7.23 (t, J=8.9 Hz, 2H); 7.50 (m, 2H); 7.87 (d, J=8.7 Hz, 2H); 8.64 (s, 1H); 11.25 (s, 1H).

Example 10

N—[(S)-2-hydroxycarbamoyl-2-(4-methane-sulphonylpiperazin-1-yl)ethyl]-4-(4-trifluoromethyl-benzyloxy)benzamide 10-1: Methyl (S)-2-(4-methanesulphonylpiperazin-1-yl)-3-[4-(4-trifluoromethylbenzyloxy)benzoylamino]-propanoate In a manner similar to example 4-5, starting from 170 mg (0.8 mmol) of methyl (S)-3-(4-hydroxybenzoylamino)-2-(4-methanesulphonylpiperazin-1-yl)propanoate (prepared as described in example 4-4) and from 160 mg (0.7 mmol) of 1-bromomethyl-4-trifluoromethylbenzene, 240 mg (100%) of methyl (S)-2-(4-methanesulphonylpiperazin-1-yl)-3-[4-(4-trifluoromethylbenzyloxy)-benzoylamino]propanoate are obtained in the form of a white solid.

10-2: (S)-2-(4-Methanesulphonylpiperazin-1-yl)-3-[4-(4-trifluoromethylbenzyloxy)benzoylamino]propanoic acid In a manner similar to example 2-5, starting from 240 mg (0.4 mmol) of methyl (S)-2-(4-methanesulphonylpiperazin- 1-yl)-3-[4-(4-trifluoromethylbenzyloxy)-benzoylamino] propanoate, 200 mg (82%) of (S)-2-(4-methanesulphonylpiperazin-1-yl)-3-[4-(4-fluorobenzyl-oxy) benzoylamino]propanoic acid are obtained in the form of a white solid.

10-3: N—[(S)-2-Hydroxycarbamoyl-2-(4-methanesulphonylpiperazin-1-yl)ethyl]-4-(4-trifluoromethylbenzyloxy)benzamide In a manner similar to example 2-6, starting from 200 mg (0.4 mmol) of (S)-2-(4-methanesulphonylpiperazin-1-yl)-3-[4-(4-trifluoromethylbenzyloxy)-benzoylamino]propanoic acid, 195 mg (95%) of N—[(S)-2-hydroxycarbamoyl-2-(4-methanesulphonylpiperazin-1-yl)-ethyl]-4-(4-trifluoromethylbenzyloxy)-benzamide are obtained in the form of a white solid having a melting point of 192° C.

$^1$H NMR (δ, DMSO): 2.60-2.73 (m, 4H); 2.84 (s, 3H); 3.01-3.10 (m, 4H); 3.35-3.45 (m, 2H); 3.52-3.60 (m, 1H); 5.29 (s, 2H); 7.08 (d, J=8 Hz, 2H); 7.67 (d, J=8.1 Hz, 2H); 7.77 (d, J=8 Hz, 2H); 7.82 (d, J=8.8 Hz, 2H); 8.34 (t, J=5.3 Hz, 1H); 8.89 (s, 1H); 10.64 (s, 1H).

Example 11

N—[(S)-2-hydroxycarbamoyl-2-(4-methane-sulphonylpiperazin-1-yl)ethyl]-4-(4-methylbenzyloxy)-benzamide

11-1: Methyl (S)-2-(4-methanesulphonylpiperazin-1-yl)-3-[4-(4-methylbenzyloxy)benzoylamino]propanoate In a manner similar to example 4-5, starting from 140 mg (0.4 mmol) of methyl (S)-3-(4-hydroxybenzoylamino)-2-(4-methanesulphonylpiperazin-1-yl)propanoate (prepared as described in example 4-4) and from 100 mg (0.5 mmol) of 1-bromomethyl-4-methylbenzene, 180 mg (100%) of methyl (S)-2-(4-methanesulphonylpiperazin-1-yl)-3-[4-(4-methylbenzyloxy)benzoylamino]propanoate are obtained in the form of a white solid.

11-2: (S)-2-(4-Methanesulphonylpiperazin-1-yl)-3-[4-(4-methylbenzyloxy)benzoylamino]propanoic acid In a manner similar to example 2-5, starting from 180 mg (0.4 mmol) of methyl (S)-2-(4-methanesulphonylpiperazin-1-yl)-3-[4-(4-methylbenzyloxy)benzoylamino]-propanoate, 140 mg (82%) of (S)-2-(4-methane-sulphonylpiperazin-1-yl)-3-[4-(4-methylbenzyloxy)-benzoylamino]propanoic acid are obtained in the form of a white solid.

11-3: N—[(S)-2-Hydroxycarbamoyl-2-(4-methanesulphonylpiperazin-1-yl)ethyl]-4-(4-methylbenzyloxy)-benzamide In a manner similar to example 2-6, starting from 140 mg (0.3 mmol) of (S)-2-(4-methanesulphonylpiperazin-1-yl)-3-[4-(4-methylbenzyloxy)benzoylamino]-propanoic acid, 100 mg (67%) of N—[(S)-2-hydroxycarbamoyl-2-(4-methanesulphonylpiperazin-1-yl)-ethyl]-4-(4-methylbenzyloxy)benzamide are obtained in the form of a white solid having a melting point of 180° C.

$^1$H NMR (δ, DMSO): 2.70 (s, 3H); 2.58-2.72 (m, 4H); 2.84 (s, 3H); 3.00-3.10 (m, 4H); 3.30 (m, 1H); 3.35-3.45 (m, 1H); 3.50-3.60 (m, 1H); 5.10 (s, 2H); 7.05 (d, J=8.8 Hz, 2H); 7.20 (d, J=7.8 Hz, 2H); 7.33 (d, J=7.9 Hz, 2H); 7.79 (d, J=8.8 Hz, 2H); 8.30 (s, 1H); 8.89 (s, 1H); 10.61 (s, 1H).

Example 12

[(S)-2-Hydroxycarbamoyl-2-(4-methane-sulphonylpiperazin-1-yl)ethyl]-2,3-dihydrobenzofuran-5-carboxamide

12-1: Methyl (S)-3-[(2,3-dihydrobenzofuran-5-carbonyl)-amino]-2-(4-methanesulphonylpiperazin-1-yl)propanoate In a manner similar to example 2-4, starting from 500 mg (1.5 mmol) of methyl (S)-3-amino-2-(4-methane-sulphonylpiperazin-1-yl)propanoate hydrochloride (prepared as described in example 2-3) and from 290 mg (1.8 mmol) of 2,3-dihydrobenzofuran-5-carboxylic acid, 410 mg (67%) of methyl (S)-3-[(2,3-dihydrobenzofuran-5-carbonyl)amino]-2-(4-methanesulphonylpiperazin-1-yl)-propanoate are obtained in the form of a colourless oil.

12-2: (S)-3-[(2,3-Dihydro-benzofuran-5-carbonyl)-amino]-2-(4-methanesulphonylpiperazin-1-yl)propanoic acid In a manner similar to example 2-5, starting from 410 mg (1 mmol) of methyl (S)-3-[(2,3-dihydrobenzofuran-5-carbonyl)amino]-2-(4-methanesulphonylpiperazin-1-yl)propanoate, 300 mg (77%) of (S)-3-[(2,3-dihydro-benzofuran-5-carbonyl)amino]-2-(4-methanesulphonylpiperazin-1-yl) propanoic acid are obtained in the form of a white solid.

12-3: [(S)-2-Hydroxycarbamoyl-2-(4-methane-sulphonylpiperazin-1-yl)ethyl]-2,3-dihydrobenzofuran-5-carboxamide In a manner similar to example 2-6, starting from 300 mg (0.8 mmol) of (S)-3-[(2,3-dihydro-benzofuran-5-carbonyl) amino]-2-(4-methanesulphonylpiperazin-1-yl)-propanoic acid, 80 mg (26%) of [(S)-2-hydroxycarbamoyl-2-(4-methanesulphonylpiperazin-1-yl)ethyl]-2,3-dihydro-benzofuran-5-carboxamide are obtained in the form of a beige solid having a melting point of 185° C.

$^1$H NMR (δ, DMSO): 2.55-2.75 (m, 4H); 2.83 (s, 3H); 3.00-3.10 (m, 4H); 3.19 (t, J=8.5 Hz, 2H); 3.33 (m, 1H); 3.43 (m, 1H); 3.55 (m, 1H); 4.57 (t, J=8.5 Hz, 2H); 6.78 (d, J=8.3 Hz, 1H); 7.50 (m, 1H); 7.65 (m, 1H); 8.27 (s, 1H); 10.67 (m, 1H).

Example 13

4-But-2-ynyloxy-N—[(S)-2-hydroxycarbamoyl-2-(4-methanesulphonylpiperazin-1-yl)ethyl]-N-methyl-benzamide

13-1: Methyl (S)-3-(tert-butoxycarbonylmethylamino)-2-(4-methanesulphonylpiperazin-1-yl)propanoate 100 mg (2.5 mmol) of 60% sodium hydride are added to a solution at 0° C. of 610 mg (1.7 mmol) of methyl (S)-3-tert-butoxycarbonylamino-2-(4-methanesulphonylpiperazin-1-yl)propanoate (prepared as described in example 2-2) in 10 ml of tetrahydrofuran. The reaction medium is stirred at ambient temperature for 30 minutes then 0.2 ml (3.3 mmol) of methyl iodide are added. After stirring for 18 h at ambient temperature, the mixture is hydrolysed then extracted with ethyl acetate. The organic phase is washed with water then with a saturated aqueous solution of sodium chloride, dried over magnesium sulphate, filtered and concentrated. The crude product obtained is purified by chromatography over silica gel eluted with a 50/50 heptane/ethyl acetate mixture. 410 mg (65%) of methyl (S)-3-(tert-butoxycarbonylmethylamino)-2-(4-methane-sulphonylpiperazin-1-yl)propanoate are obtained in the form of a colourless oil.

13-2: Methyl ((S)-3-amino)-2-(4-methanesulphonylpiperazin-1-yl)propanoate hydrochloride In a manner similar to example 2-3, starting from 410 mg (1.1 mmol) of methyl (S)-3-(tert-butoxycarbonylmethylamino)-2-(4-methanesulphonylpiperazin-1-yl)-propanoate, 320 mg (94%) of methyl ((S)-3-amino)-2-(4-methanesulphonylpiperazin-1-yl)propanoate hydrochloride are obtained in the form of a beige solid.

13-3: Methyl (S)-3-[(4-but-2-ynyloxybenzoyl)methylamino]-2-(1-methanesulphonylpiperidin-4-yl)propanoate In a manner similar to example 2-4, starting from 320 mg (1 mmol) of methyl ((S)-3-amino)-2-(4-methane-sulphonylpiperazin-1-yl)propanoate hydrochloride and from 210 mg (1.1 mmol) of 4-but-2-ynyloxybenzoic acid (prepared as described in example 1-5); 340 mg (74%) of methyl (S)-3-[(4-but-2-ynyloxybenzoyl)methylamino]-2-(1-methanesulphonylpiperidin-4-yl)propanoate are obtained in the form of a white solid.

13-4: (S)-3-[(4-But-2-ynyloxybenzoyl)methylamino]-2-(4-methanesulphonylpiperazin-1-yl)propanoic acid In a manner similar to example 2-5, starting from 340 mg (0.8 mmol) of methyl (S)-3-[(4-but-2-ynyloxy-benzoyl)methylamino]-2-(1-methanesulphonylpiperidin-4-yl)propanoate, 260 mg (81%) of (S)-3-[(4-but-2-ynyloxy-benzoyl)methylamino]-2-(4-methanesulphonylpiperazin-1-yl)propanoic acid are obtained in the form of a white solid.

13-5: 4-But-2-ynyloxy-N—[(S)-2-hydroxycarbamoyl-2-(4-methanesulphonylpiperazin-1-yl)ethyl]-N-methylbenzamide In a manner similar to example 2-6, starting from 260 mg (0.6 mmol) of (S)-3-[(4-but-2-ynyloxybenzoyl)-methylamino]-2-(4-methanesulphonylpiperazin-1-yl)-propanoic acid, 70 mg (26%) of 4-but-2-ynyloxy-N—[(S)-2-hydroxycarbamoyl-2-(4-methanesulphonylpiperazin-1-yl)ethyl]-N-methylbenzamide are obtained in the form of a white solid having a melting point of 145° C.
$^1$H NMR (δ, DMSO): 1.83 (s, 3H); 2.34 (m, 1H); 2.52-2.75 (m, 3H); 2.85 (s, 3H); 2.90 (s, 3H); 2.90-3.10 (m, 4H); 3.35-3.45 (m, 3H); 4.79 (s, 2H); 7.00 (d, J=8.6 Hz, 2H); 7.35 (d, J=6.2 Hz, 2H); 8.98 (s, 1H); 10.70 (s, 1H).

Example 14

N—[(S)-2-Hydroxycarbamoyl-2-(4-methane-sulphonylpiperazin-1-yl)ethyl]-4-(2-methylquinolin-4-ylmethoxy)benzamide

14-1: Methyl (S)-2-(4-methanesulphonylpiperazin-1-yl)-3-[4-(2-methylquinolin-4-ylmethoxy)benzoylamino]-propanoate In a manner similar to example 4-5, starting from 400 mg (1 mmol) of methyl (S)-3-(4-hydroxybenzoylamino)-2-(4-methanesulphonylpiperazin-1-yl)propanoate (prepared as described in example 4-4) and from 240 mg (1.2 mmol) of 4-chloromethyl-2-methylquinoline, 460 mg (82%) of methyl (S)-2-(4-methanesulphonylpiperazin-1-yl)-3-[4-(2-methylquinolin-4-ylmethoxy)benzoylamino]-propanoate are obtained in the form of a white solid.

14-2: ((S)-2-(4-Methanesulphonylpiperazin-1-yl)-3-[4-(2-methylquinolin-4-ylmethoxy)benzoylamino] propanoic acid In a manner similar to example 2-5, starting from 460 mg (0.85 mmol) of methyl (S)-2-(4-methanesulphonylpiperazin-1-yl)-3-[4-(2-methylquinolin-4-ylmethoxy)-benzoylamino] propanoate, 370 mg (82%) of ((S)-2-(4-methanesulphonylpiperazin-1-yl)-3-[4-(2-methylquinolin-4-ylmethoxy) benzoylamino]propanoic acid are obtained in the form of a white solid.

14-3: N—[(S)-2-Hydroxycarbamoyl-2-(4-methanesulphonylpiperazin-1-yl)ethyl]-4-(2-methylquinolin-4-ylmethoxy)-benzamide In a manner similar to example 2-6, starting from 370 mg (0.7 mmol) of ((S)-2-(4-methanesulphonylpiperazin-1-yl)-3-[4-(2-methylquinolin-4-ylmethoxy)-benzoylamino]propanoic acid, 280 mg (74%) of N—[(S)-2-hydroxycarbamoyl-2-(4-methanesulphonylpiperazin-1-yl)-ethyl]-4-(2-methylquinolin-4-ylmethoxy)benzamide are obtained in the form of a beige solid having a melting point of 175° C.
$^1$H NMR (δ, DMSO): 2.63 (s, 3H); 2.65-2.75 (m, 4H); 2.83 (s, 3H); 2.98-3.10 (m, 4H); 3.34 (m, 1H); 3.40-3.50 (m, 1H); 3.52-3.62 (m, 1H); 5.67 (s, 2H); 7.20 (d, J=7.8 Hz, 2H); 7.55-7.60 (m, 2H); 7.74 (t, J=7.2 Hz, 1H); 7.87 (d, J=8.3 Hz, 2H); 7.97 (d, J=8.3 Hz, 1H); 8.10 (d, J=8.1 Hz, 1H); 8.41 (s, 1H); 8.94 (s, 1H); 10.71 (s, 1H).

Example 15

N—[(S)-2-Hydroxycarbamoyl-2-(4-methane-sulphonylpiperazin-1-yl)ethyl]-4-(naphthalen-1-yl-methoxy)benzamide

15-1: Methyl (S)-2-(4-methanesulphonylpiperazin-1-yl)-3-[4-(naphthalen-1-ylmethoxy)benzoylamino] propanoate In a manner similar to example 4-5, starting from 300 mg (0.8 mmol) of methyl (S)-3-(4-hydroxybenzoylamino)-2-(4-methanesulphonylpiperazin-1-yl)-propanoate (prepared as described in example 4-4) and from 200 mg (1.2 mmol) of 1-bromomethylnaphthalene, 320 mg (78%) of methyl (S)-2-(4-methanesulphonylpiperazin-1-yl)-3-[4-(2-methylquinolin-4-ylmethoxy)benzoylamino]-propanoate are obtained in the form of a white solid.

15-2: (S)-2-(4-Methanesulphonylpiperazin-1-yl)-3-[4-(naphthalen-1-ylmethoxy)benzoylamino]propanoic acid In a manner similar to example 2-5, starting from 320 mg (0.6 mmol) of methyl (S)-2-(4-methanesulphonylpiperazin-1-yl)-3-[4-(2-methylquinolin-4-ylmethoxy)-benzoylamino] propanoate, 270 mg (87%) of (S)-2-(4-methanesulphonylpiperazin-1-yl)-3-[4-(naphthalen-1-ylmethoxy) benzoylamino]propanoic acid are obtained in the form of a white solid.

15-3: N—[(S)-2-Hydroxycarbamoyl-2-(4-methanesulphonylpiperazin-1-yl)ethyl]-4-(naphthalen-1-ylmethoxy)-benzamide In a manner similar to example 2-6, starting from 270 mg (0.5 mmol) of (S)-2-(4-methanesulphonylpiperazin-1-yl)-3-[4-(naphthalen-1-ylmethoxy)benzoyl-amino]propanoic acid, 100 mg (36%) of N—[(S)-2-hydroxycarbamoyl-2-(4-methanesulphonylpiperazin-1-yl)ethyl]-4-(naphthalen-1-ylmethoxy)benzamide are obtained in the form of a beige solid having a melting point of 170° C.

$^1$H NMR (δ, DMSO): 2.60-2.75 (m, 4H); 2.84 (s, 3H); 3.00-3.15 (m, 4H); 3.34 (m, 1H); 3.41 (m, 1H); 3.57 (m, 1H); 5.62 (s, 2H); 7.16 (d, J=8.6 Hz, 2H); 7.45-7.60 (m, 3H); 7.69 (d, J=6.9 Hz, 1H); 7.84 (d, J=8.5 Hz, 2H); 7.90-8.00 (m, 2H); 8.08 (d, J=7.6 Hz, 1H); 8.34 (s, 1H); 8.90 (s, 1H); 10.63 (s, 1H).

Example 16

4-(4-Hydroxybut-2-ynyloxy)-N—[(S)-2-hydroxycarbamoyl-2-(4-methanesulphonylpiperazin-1-yl)-ethyl]benzamide

16-1: Methyl (S)-3-{4-[4-(tert-butyldimethylsilanyloxy)but-2-ynyloxy]benzoylamino}-2-(4-methanesulphonylpiperazin-1-yl)propanoate In a manner similar to example 4-5, starting from 400 mg (1 mmol) of methyl (S)-3-(4-hydroxybenzoylamino)-2-(4-methanesulphonylpiperazin-1-yl)propanoate (prepared as described in example 4-4) and from 270 mg (1.2 mmol) of tert-butyl(4-chloro-but-2-ynyloxy)-dimethylsilane; 510 mg (88%) of methyl (S)-3-{4-[4-(tert-butyldimethylsilanyloxy)but-2-ynyloxy]benzoyl-amino}-2-(4-methanesulphonylpiperazin-1-yl)propanoate are obtained in the form of a colourless oil.

16-2: (S)-3-[4-(4-Hydroxy-but-2-ynyloxy)benzoylamino]-2-(4-methanesulphonylpiperazin-1-yl)propanoic acid In a manner similar to example 2-5, starting from 510 mg (0.9 mmol) of methyl (S)-3-{4-[4-(tert-butyl-dimethylsilanyloxy)but-2-ynyloxy]benzoylamino}-2-(4-methanesulphonylpiperazin-1-yl)propanoate, 205 mg (52%) of (S)-3-[4-(4-hydroxybut-2-ynyloxy)benzoylamino]-2-(4-methanesulphonylpiperazin-1-yl)propanoic acid are obtained in the form of a white solid.

16-3: 4-(4-Hydroxybut-2-ynyloxy)-N—[(S)-2-hydroxycarbamoyl-2-(4-methanesulphonylpiperazin-1-yl)ethyl]-benzamide In a manner similar to example 2-6, starting from 205 mg (0.5 mmol) of (S)-3-[4-(4-hydroxybut-2-ynyloxy)-benzoylamino]-2-(4-methanesulphonylpiperazin-1-yl)-propanoic acid, 40 mg (19%) of 4-(4-hydroxybut-2-ynyloxy)-N—[(S)-2-hydroxycarbamoyl-2-(4-methane-sulphonylpiperazin-1-yl)ethyl]benzamide are obtained in the form of a beige solid having a melting point of 162° C.

$^1$H NMR (δ, DMSO): 2.55-2.70 (m, 4H); 2.80 (s, 3H); 2.90-3.00 (m, 4H); 3.38 (m, 3H); 4.10 (s, 2H); 4.88 (s, 2H); 5.25 (s, 1H); 7.00-7.05 (m, 2H); 7.80-7.82 (d, J=8.8 Hz, 2H).

Example 17

N—[(S)-2-Hydroxycarbamoyl-2-(4-methane-sulphonylpiperazin-1-yl)ethyl]-4-(4-methoxybenzyloxy)-benzamide

17-1: Methyl (S)-2-(4-methanesulphonylpiperazin-1-yl)-3-[4-(4-methoxybenzyloxy)benzoylamino]propanoate In a manner similar to example 4-5, starting from 300 mg (0.8 mmol) of methyl (S)-3-(4-hydroxybenzoylamino)-2-(4-methanesulphonylpiperazin-1-yl)propanoate (prepared as described in example 4-4) and from 0.14 ml (0.9 mmol) of 1-bromomethyl-4-methoxybenzene; 390 mg (100%) of methyl (S)-2-(4-methanesulphonylpiperazin-1-yl)-3-[4-(4-methoxybenzyloxy)benzoylamino]propanoate are obtained in the form of a colourless oil.

17-2: (S)-2-(4-Methanesulphonylpiperazin-1-yl)-3-[4-(4-methoxybenzyloxy)benzoylamino]propanoic acid In a manner similar to example 2-5, starting from 390 mg (0.8 mmol) of methyl (S)-2-(4-methanesulphonylpiperazin-1-yl)-3-[4-(4-methoxybenzyloxy)benzoylamino]-propanoate, 343 mg (90%) of (S)-2-(4-methanesulphonylpiperazin-1-yl)-3-[4-(4-methoxybenzyloxy)benzoylamino]-propanoic acid are obtained in the form of a white solid.

17-3: N—[(S)-2-Hydroxycarbamoyl-2-(4-methanesulphonylpiperazin-1-yl)ethyl]-4-(4-methoxy-benzyloxy)benzamide In a manner similar to example 2-6, starting from 343 mg (0.7 mmol) of (S)-2-(4-methanesulphonylpiperazin-1-yl)-3-[4-(4-methoxybenzyloxy)benzoylamino]-propanoic acid, 70 mg (20%) of N—[(S)-2-hydroxycarbamoyl-2-(4-methane-sulphonylpiperazin-1-yl)-ethyl]-4-(4-methoxybenzyloxy) benzamide are obtained in the form of a white solid having a melting point of 148° C.

$^1$H NMR (δ, DMSO): 2.94 (s, 3H); 2.98-3.10 (m, 2H); 3.15-3.40 (m, 8H); 3.50-3.60 (m, 1H); 3.76 (s, 3H); 5.08 (s, 2H); 6.94 (, 2H); 7.06 (m, 2H); 7.37 (m, 2H); 7.84 (m, 2H); 8.54 (s, 1H); 9.25 (m, 1H); 11.09 (m, 1H).

Example 18

N—[(S)-2-Hydroxycarbamoyl-2-(4-methane-sulphonylpiperazin-1-yl)ethyl]-4-(pyridin-4-ylmethoxy)-benzamide

18-1: Methyl (S)-2-(4-methanesulphonylpiperazin-1-yl)-3-[4-(pyridin-4-ylmethoxy)benzoylamino]propanoate 1 g (3.2 mmol) of caesium carbonate and 280 mg (1.7 mmol) of 4-chloromethylpyridine hydrochloride are added to a solution of 560 mg (1.4 mmol) of methyl (S)-3-(4-hydroxybenzoylamino)-2-(4-methanesulphonylpiperazin-1-yl)propanoate (prepared as described in example 4-4) diluted in 20 ml of dimethylformamide. The reaction medium is stirred at 80° C. for 24 h. The reaction medium is cooled, hydrolysed and extracted with ethyl acetate. The organic phase is washed once with water and once with a saturated aqueous solution of sodium chloride, dried over magnesium sulphate, filtered and concentrated under vacuum. The crude product is purified by chromatography over silica gel eluted with a 30/70 heptane/ethyl acetate mixture+10% methanol. 430 mg (62%) of methyl (S)-2-(4-methane-sulphonylpiperazin-1-yl)-3-[4-(pyridin-4-ylmethoxy)-benzoylamino]propanoate are obtained in the form of a white solid.

18-2: (S)-2-(4-Methanesulphonylpiperazin-1-yl)-3-[4-(pyridin-4-ylmethoxy)benzoylamino]propanoic acid In a manner similar to example 2-5, starting from 430 mg (0.9 mmol) of methyl (S)-2-(4-methanesulphonylpiperazin-1-yl)-3-[4-(pyridin-4-ylmethoxy)benzoyl-amino]propanoate, 360 mg (86%) of (S)-2-(4-methane-sulphonylpiperazin-1-yl)-3-[4-(pyridin-4-ylmethoxy)-benzoylamino]propanoic acid are obtained in the form of a white solid.

18-3: N—[(S)-2-Hydroxycarbamoyl-2-(4-methanesulphonylpiperazin-1-yl)ethyl]-4-(pyridin-4-ylmethoxy)benzamide In a manner similar to example 2-6, starting from 360 mg (0.8 mmol) of (S)-2-(4-methanesulphonylpiperazin-1-yl)-3-[4-(pyridin-4-ylmethoxy)benzoyl-amino]propanoic acid, 230 mg (62%) of N—[(S)-2-hydroxycarbamoyl-2-(4-methanesulphonylpiperazin-1-yl)ethyl]-4-(pyridin-4-ylmethoxy)benzamide are obtained in the form of a white solid having a melting point of 213° C.
$^1$H NMR (δ, DMSO): 2.55-2.70 (m, 4H); 2.84 (s, 3H); 3.02-3.09 (m, 4H); 3.35-3.50 (m, 2H); 3.50-3.60 (m, 1H); 5.26 (s, 2H); 7.07 (d, J=8.9 Hz, 2H); 7.44 (d, J=5.9 Hz, 2H); 7.83 (d, J=8.8 Hz, 2H); 8.36 (m, 1H); 8.58 (d, J=8 Hz, 2H); 8.89 (s, 1H); 10.67 (s, 1H).

Example 19

N—[(S)-2-Hydroxycarbamoyl-2-(4-methane-sulphonylpiperazin-1-yl)ethyl]-4-(2-methylnaphthalen-1-ylmethoxy)benzamide

19-1: Methyl (S)-2-(4-methanesulphonylpiperazin-1-yl)-3-[4-(2-methyl-naphthalen-1-ylmethoxy)benzoylamino]-propanoate In a manner similar to example 18-1, starting from 400 mg (1 mmol) of methyl (S)-3-(4-hydroxybenzoylamino)-2-(4-methanesulphonylpiperazin-1-yl)propanoate (prepared as described in example 4-4) and from 198 mg (1.1 mmol) of 1-chloromethyl-2-methylnaphtalene, 259 mg (90%) of methyl (S)-2-(4-methanesulphonylpiperazin-1-yl)-3-[4-(2-methylnaphthalen-1-ylmethoxy)benzoylamino]-propanoate are obtained in the form of a white solid.

19-2: (S)-2-(4-Methanesulphonylpiperazin-1-yl)-3-[4-(2-methylnaphthalen-1-ylmethoxy)benzoylamino]propanoic acid In a manner similar to example 2-5, starting from 259 mg (0.5 mmol) of methyl (S)-2-(4-methanesulphonylpiperazin-1-yl)-3-[4-(2-methylnaphthalen-1-ylmethoxy)-benzoylamino]propanoate, 227 mg (90%) of (S)-2-(4-methanesulphonylpiperazin-1-yl)-3-[4-(2-methyl-naphthalen-1-ylmethoxy)benzoylamino]propanoic acid are obtained in the form of a white solid.

19-3: N—[(S)-2-Hydroxycarbamoyl-2-(4-methanesulphonylpiperazin-1-yl)ethyl]-4-(2-methylnaphthalen-1-yl-methoxy)benzamide In a manner similar to example 2-6, starting from 222 mg (46%) of (S)-2-(4-methanesulphonylpiperazin-1-yl)-3-[4-(2-methylnaphthalen-1-ylmethoxy)benzoylamino]-propanoic acid, 104 mg (46%) of N—[(S)-2-hydroxycarbamoyl-2-(4-methanesulphonylpiperazin-1-yl)ethyl]-4-(2-methylnaphthalen-1-ylmethoxy)benzamide are obtained in the form of a white solid having a melting point of 155° C.
$^1$H NMR (δ, DMSO): 2.45 (s, 3H); 2.59 (m, 4H); 2.76 (s, 3H); 2.97 (m, 4H); 3.26 (m, 1H); 3.32 (m, 1H); 3.49 (m, 1H); 5.47 (s, 2H); 7.08 (d, J=8.7 Hz, 2H); 7.39 (m, 3H); 7.81 (m, 4H); 7.94 (d, J=8.36 Hz, 1H); 8.25 (m, 1H); 8.81 (m, 1H); 10.54 (s, 1H).

Example 20

N—[(R)-2-Hydroxycarbamoyl-2-(4-methane-sulphonylpiperazin-1-yl)ethyl]-4-(2-methylquinolin-4-ylmethoxy)benzamide

20-1: Methyl (R)-3-tert-butoxycarbonylamino-2-(4-methanesulphonylpiperazin-1-yl)propanoate In a manner similar to example 2-2, starting from 6 g (23.6 mmol) of methyl (R)-2-amino-3-tert-butoxycarbonylamino-propanoate hydrochloride and from 5.2 g (23.6 mmol) of N,N-bis(2-chloroethyl)methanesulphonamide (prepared as described in example 2-1), 3.8 g (44%) of methyl (R)-3-tert-butoxycarbonylamino-2-(4-methanesulphonylpiperazin-1-yl)propanoate are obtained in the form of a light-yellow solid.

20-2: Methyl (R)-3-amino-2-(4-methanesulphonylpiperazin-1-yl)propanoate dihydrochloride In a manner similar to example 2-3, starting from 3.8 g (10.4 mmol) of methyl (R)-3-tert-butoxycarbonylamino-2-(4-methanesulphonylpiperazin-1-yl)propanoate, 3 g (97%) of methyl (R)-3-amino-2-(4-methanesulphonylpiperazin-1-yl)propanoate dihydrochloride are obtained in the form of a beige solid.

20-3: Methyl (R)-2-(4-methanesulphonylpiperazin-1-yl)-3-[4-(2-methoxyethoxymethoxy)benzoylamino]propanoate In a manner similar to example 4-3, starting from 560 mg (1.7 mmol) of methyl (R)-3-amino-2-(4-methanesulphonylpiperazin-1-yl)propanoate dihydrochloride and 500 mg (1.5 mmol) of 4-(2-methoxyethoxymethoxy)benzoic acid (prepared as described in example 4-2), 600 mg (85%) of methyl (R)-2-(4-methanesulphonylpiperazin-1-yl)-3-[4-(2-methoxyethoxymethoxy)benzoylamino]propanoate are obtained in the form of a white solid.

20-4: Methyl (R)-3-(4-hydroxybenzoylamino)-2-(4-methanesulphonylpiperazin-1-yl)propanoate In a manner similar to example 4-4, starting from 600 mg (1.3 mmol) of methyl (R)-2-(4-methanesulphonylpiperazin-1-yl)-3-[4-(2-methoxyethoxymethoxy)benzoyl-amino]propanoate, 400 mg (100%) of methyl (R)-3-(4-hydroxybenzoylamino)-2-(4-methanesulphonylpiperazin-1-yl)propanoate are obtained in the form of a white solid.

20-5: Methyl (R)-2-(4-methanesulphonylpiperazin-1-yl)-3-[4-(2-methylquinolin-4-ylmethoxy)benzoylamino]-propanoate In a manner similar to example 18-1, starting from 400 mg (1 mmol) of methyl (R)-3-(4-hydroxybenzoylamino)-2-(4-methanesulphonylpiperazin-1-yl)propanoate and from 211 mg (1.1 mmol) of 4-chloromethyl-2-methylquinoline, 330 mg (60%) of methyl (R)-2-(4-methane-sulphonylpiperazin-1-yl)-3-[4-(2-methylquinolin-4-yl-methoxy)benzoylamino]propanoate are obtained in the form of a white solid.

20-6: (R)-2-(4-Methanesulphonylpiperazin-1-yl)-3-[4-(2-methylquinolin-4-ylmethoxy)benzoylamino]propanoic acid In a manner similar to example 2-5, starting from 290 mg (0.5 mmol) of methyl (R)-2-(4-methanesulphonylpiperazin-1-yl)-3-[4-(2-methylquinolin-4-ylmethoxy)-benzoylamino]propanoate, 240 mg (86%) of (R)-2-(4-methanesulphonylpiperazin-1-yl)-3-[4-(2-methylquinolin-4-ylmethoxy)benzoylamino]propanoic acid are obtained in the form of a white solid.

20-7: N—[(R)-2-Hydroxycarbamoyl-2-(4-methane-sulphonylpiperazin-1-yl)ethyl]-4-(2-methylquinolin-4-ylmethoxy)-benzamide In a manner similar to example 2-6, starting from 250 mg (0.5 mmol) of (R)-2-(4-methanesulphonylpiperazin-1-yl)-3-[4-(2-methylquinolin-4-ylmethoxy)-benzoylamino]propanoic acid, 89 mg (33%) of N—[(R)-2-hydroxycarbamoyl-2-(4-methanesulphonylpiperazin-1-yl)-ethyl]-4-(2-methylquinolin-4-ylmethoxy)benzamide are obtained in the form of a white solid.

$^1$H NMR (δ, DMSO): 2.35 (m, 2H); 2.60 (m, 2H); 2.88 (m, 6H); 3.17 (m, 4H); 3.55 (m, 2H); 3.70 (m, 1H); 5.88 (s, 2H); 7.30 (d, J=8.6 Hz, 2H); 7.84-7.98 (m, 4H); 8.02 (m, 1H); 8.17 (d, J=8.3 Hz, 1H); 8.37 (d, J=8.04 Hz, 1H); 8.48 (s, 1H); 9.11 (m, 1H); 10.85 (m, 1H).

Example 21

N—[(S)-2-hydroxycarbamoyl-2-(4-methane-sulphonylpiperazin-1-yl)ethyl]-4-(quinolin-4-ylmethoxy)benzamide

21-1: Methyl (S)-2-(4-methanesulphonylpiperazin-1-yl)-3-[4-(quinolin-4-ylmethoxy)benzoylamino]propanoate In a manner similar to example 18-1, starting from 400 mg (1 mmol) of methyl (S)-3-(4-hydroxy-benzoyl-amino)-2-(4-methanesulphonylpiperazin-1-yl)propanoate (prepared as described in example 4-4) and from 203 mg (1.1 mmol) of 4-(chloromethyl)quinoline, 363 mg (66%) of methyl (S)-2-(4-methanesulphonylpiperazin-1-yl)-3-[4-(quinolin-4-ylmethoxy)benzoylamino]propanoate are obtained in the form of a pale yellow solid.

21-2: (S)-2-(4-Methanesulphonylpiperazin-1-yl)-3-[4-(quinolin-4-ylmethoxy)benzoylamino]propanoic acid In a manner similar to example 2-5, starting from 362 mg (0.7 mmol) of methyl (S)-2-(4-methanesulphonylpiperazin-1-yl)-3-[4-(quinolin-4-ylmethoxy)benzoyl-amino]propanoate, 326 mg (92%) of (S)-2-(4-methane-sulphonylpiperazin-1-yl)-3-[4-(quinolin-4-ylmethoxy)-benzoylamino] propanoic acid.

21-3: N—[(S)-2-Hydroxycarbamoyl-2-(4-methane-sulphonylpiperazin-1-yl)ethyl]-4-(quinolin-4-ylmethoxy)benzamide In a manner similar to example 2-6, starting from 211 mg (0.6 mmol) of (S)-2-(4-methanesulphonylpiperazin-1-yl)-3-[4-(quinolin-4-ylmethoxy)benzoyl-amino]propanoic acid, 36 mg (11%) of N—[(S)-2-hydroxycarbamoyl-2-(4-methanesulphonylpiperazin-1-yl)ethyl]-4-(quinolin-4-yl-methoxy)benzamide are obtained in the form of a beige powder.

$^1$H NMR (δ, DMSO): 2.66 (m, 4H); 2.85 (s, 3H); 3.06 (m, 5H); 3.42 (m, 1H); 3.55 (m, 1H); 5.75 (s, 2H); 7.21 (d, J=8.8 Hz, 2H); 7.67 (m, 2H); 7.83 (m, 3H); 8.09 (d, J=8.3 Hz, 1H); 8.19 (t, J=8 Hz, 1H); 8.34 (d, J=4.9 Hz, 1H); 8.92 (d, J=4.3 Hz, 2H); 10.63 (s, 1H).

Example 22

N—[(S)-2-(4-Benzylpiperazin-1-yl)-2-hydroxycarbamoylethyl]-4-(2-methylquinolin-4-yl-methoxy)benzamide

22-1: Benzyl-bis(2-iodoethyl)amine 5.7 ml (37.2 mmol) of triethylamine are added to a solution of 10 g (37.2 mmol) of benzyl-bis(2-chloroethyl)amine hydrochloride in 300 ml of acetone. The reaction medium is stirred at 40° C. for 30 minutes then brought to ambient temperature and filtered. 16.8 g (111.6 mmol) of sodium iodide are added to the filtrate then the reaction medium is heated at reflux for 29 h. 11.2 g (74.4 mmol) of sodium iodide are added and the mixture is heated at 50° C. for 18 h. The acetone is evaporated and the residue is hydrolysed and extracted with ethyl acetate. The organic phase is washed with water then with a saturated aqueous solution of sodium chloride, dried over magnesium sulphate and concentrated under vacuum. The crude product is purified by chromatography over silica gel eluted with a 50/50 heptane/ethyl acetate mixture. 9.6 g (63%) of benzyl-bis(2-iodoethyl)amine are obtained in the form of a yellow oil.

22-2: Methyl (S)-2-(4-benzylpiperazin-1-yl)-3-tert-butoxycarbonylaminopropanoate In a manner similar to example 2-2, starting from 5.9 g (23 mmol) of methyl (S)-2-amino-3-tert-butoxycarbonylamino-propanoate hydrochloride and 9.6 g (23 mmol) of benzyl-bis(2-iodoethyl)amine, 5.6 g (64%) of methyl (S)-2-(4-benzylpiperazin-1-yl)-3-tert-butoxycarbonylaminopropanoate are obtained in the form of a yellow oil.

22-3: Methyl (S)-3-amino-2-(4-benzylpiperazin-1-yl)-propanoate trihydrochloride In a manner similar to example 2-3, starting from 5.6 g (14.8 mmol) of methyl (S)-2-(4-benzylpiperazin-1-yl)-3-tert-butoxycarbonylaminopropanoate, 5 g (88%) of methyl (S)-3-amino-2-(4-benzylpiperazin-1-yl)propanoate trihydrochloride are obtained in the form of a beige solid.

22-4: Methyl (S)-2-(4-benzylpiperazin-1-yl)-3-[4-(2-methoxyethoxymethoxy)benzoylamino]propanoate In a manner similar to example 4-3, starting from 3.2 g (14.2 mmol) of 4-(2-methoxyethoxymethoxy)benzoic acid (prepared as described in example 4-2) and from 5 g (12.9 mmol) of methyl (S)-3-amino-2-(4-benzylpiperazin-1-yl) propanoate trihydrochloride, 6.4 g (100%) of methyl (S)-2-(4-benzylpiperazin-1-yl)-3-[4-(2-methoxy-ethoxymethoxy) benzoylamino]propanoate are obtained in the form of a colourless oil.

22-5: Methyl (S)-2-(4-benzylpiperazin-1-yl)-3-(4-hydroxybenzoylamino)propanoate In a manner similar to example 4-4, starting from 1.1 g (2.3 mmol) of methyl (S)-2-(4-benzylpiperazin-1-yl)-3-[4-(2-methoxyethoxymethoxy)benzoylamino]propanoate, 0.71 g (79%) of methyl (S)-2-(4-benzylpiperazin-1-yl)-3-(4-hydroxybenzoylamino)propanoate is obtained in the form of a white solid.

22-6: Methyl (S)-2-(4-benzylpiperazin-1-yl)-3-[4-(2-methylquinolin-4-ylmethoxy)benzoylamino]propanoate In a manner similar to example 18-1, starting from 0.5 g (2.2 mmol) 4-chloromethyl-2-methylquinoline hydrochloride and from 0.7 g (1.8 mmol) of methyl (S)-2-(4-benzylpiperazin-1-yl)-3-(4-hydroxybenzoylamino)-propanoate in 20 ml of 2-butanone, 0.7 g (75%) of methyl (S)-2-(4-benzylpiperazin-1-yl)-3-[4-(2-methylquinolin-4-ylmethoxy)benzoylamino]propanoate is obtained in the form of an orange solid.

22-7: (S)-2-(4-Benzylpiperazin-1-yl)-3-[4-(2-methylquinolin-4-ylmethoxy)benzoylamino]propanoic acid In a manner similar to example 2-5, starting from 0.7 g (1.3 mmol) of methyl (S)-2-(4-benzylpiperazin-1-yl)-3-[4-(2-methylquinolin-4-ylmethoxy)benzoylamino]-propanoate, 0.7 g (92%) of (S)-2-(4-benzylpiperazin-1-yl)-3-[4-(2-methylquinolin-4-ylmethoxy)benzoylamino]-propanoic acid is obtained in the form of a beige solid.

22-8: N—[(S)-2-(4-Benzylpiperazin-1-yl)-2-hydroxycarbamoylethyl]-4-(2-methylquinolin-4-ylmethoxy)-benzamide In a manner similar to example 2-6, starting from 0.7 g (1.2 mmol) of (S)-2-(4-benzylpiperazin-1-yl)-3-[4-(2-methylquinolin-4-ylmethoxy)benzoylamino]propanoic acid, 120 mg (19%) of N—[(S)-2-(4-benzylpiperazin-1-yl)-2-hydroxycarbamoylethyl]-4-(2-methylquinolin-4-yl-methoxy) benzamide are obtained in the form of a beige solid having a melting point of 169° C.

$^{1}$H NMR (δ, DMSO): 2.37 (m, 4H); 2.62 (m, 4H); 2.71 (s, 3H); 3.28 (t, J=7 Hz, 1H); 3.45 (m, 3H); 3.57 (m, 1H); 5.72 (s, 2H); 7.19-7.40 (m, 7H); 7.62 (m, 2H); 7.80 (t, J=7.2 Hz, 1H); 7.88 (d, J=8 Hz, 2H); 8.02 (d, J=8 Hz, 1H); 8.15 (d, J=8 Hz, 1H); 8.30 (m, 1H); 8.88 (s, 1H); 10.59 (s, 1H).

Example 23

N-{(S)-2-Hydroxycarbamoyl-2-[4-(propane-2-sulphonyl)piperazin-1-yl]ethyl}-4-(2-methylquinolin-4-ylmethoxy)benzamide

23-1: Methyl (S)-3-[4-(2-methoxyethoxymethoxy) benzoyl-amino]-2-piperazin-1-ylpropanoate 520 mg of 10 wt % palladium on carbon are added to a solution of 5.2 g (10.7 mmol) of methyl (S)-2-(4-benzylpiperazin-1-yl)-3-[4-(2-methoxyethoxymethoxy)-benzoylamino]propanoate (prepared as described in example 22-4) in 80 ml of ethanol previously degassed under a stream of nitrogen, and the mixture is placed under hydrogen at atmospheric pressure. After stirring for 18 h at ambient temperature, the reaction medium is filtered over celite. The filtrate is concentrated to give 3.8 g (90%) of methyl (S)-3-[4-(2-methoxyethoxy-methoxy)benzoylamino]-2-piperazin-1-ylpropanoate in the form of a colourless oil.

23-2: Methyl (S)-3-[4-(2-methoxyethoxymethoxy) benzoyl-amino]-2-[4-(propane-2-sulphonyl)piperazin-1-yl]-propanoate In a manner similar to example 2-1, starting from 0.2 ml (1.9 mmol) of 2-propanesulphonyl chloride and from 0.7 g (1.8 mmol) of methyl (S)-3-[4-(2-methoxy-ethoxymethoxy) benzoylamino]-2-piperazin-1-ylpropanoate, 0.6 g (68%) of methyl (S)-3-[4-(2-methoxyethoxy-methoxy)benzoylamino]-2-[4-(propane-2-sulphonyl)-piperazin-1-yl]propanoate is obtained in the form of a colourless oil.

23-3: Methyl (S)-3-(4-hydroxybenzoylamino)-2-[4-(propane-2-sulphonyl)piperazin-1-yl]propanoate In a manner similar to example 4-4, starting from 600 mg (1.2 mmol) of methyl (S)-3-[4-(2-methoxyethoxy-methoxy) benzoylamino]-2-[4-(propane-2-sulphonyl)-piperazin-1-yl] propanoate, 500 mg (100%) of methyl (S)-3-(4-hydroxybenzoylamino)-2-[4-(propane-2-sulphonyl)-piperazin-1-yl] propanoate are obtained in the form of a white solid.

23-4: Methyl (S)-3-[4-(2-methylquinolin-4-yl-methoxy)-benzoylamino]-2-[4-(propane-2-sulphonyl)piperazin-1-yl]propanoate In a manner similar to example 18-1, starting from 500 mg (1.2 mmol) of methyl (S)-3-(4-hydroxybenzoylamino)-2-[4-(propane-2-sulphonyl)piperazin-1-yl]-propanoate and from 300 mg (1.5 mmol) of 4-chloromethyl-2-methylquinoline hydrochloride, 560 mg (81%) of methyl (S)-3-[4-(2-methylquinolin-4-yl-methoxy)benzoylamino]-2-[4-(propane-2-sulphonyl)-piperazin-1-yl]propanoate are obtained in the form of a beige solid.

23-5: (S)-3-[4-(2-Methylquinolin-4-ylmethoxy)benzoyl-amino]-2-[4-(propane-2-sulphonyl)piperazin-1-yl]-propanoic acid In a manner similar to example 2-5, starting from 560 mg (1 mmol) of methyl (S)-3-[4-(2-methylquinolin-4-yl-methoxy)benzoylamino]-2-[4-(propane-2-sulphonyl)-piperazin-1-yl]propanoate, 490 mg (91%) of (S)-3-[4-(2-methylquinolin-4-ylmethoxy)benzoylamino]-2-[4-(propane-2-sulphonyl)piperazin-1-yl]propanoic acid are obtained in the form of a white solid.

23-6: N—{(S)-2-Hydroxycarbamoyl-2-[4-(propane-2-sulphonyl)piperazin-1-yl]-ethyl}-4-(2-methylquinolin-4-ylmethoxy)benzamide In a manner similar to example 2-6, starting from 490 mg (0.9 mmol) of (S)-3-[4-(2-methylquinolin-4-yl-methoxy) benzoylamino]-2-[4-(propane-2-sulphonyl)-piperazin-1-yl] propanoic acid, 250 mg (50%) of N-{(S)-2-hydroxycarbam-oyl-2-[4-(propane-2-sulphonyl)piperazin-1-yl]-ethyl}-4-(2- methylquinolin-4-ylmethoxy)benzamide are obtained in the form of a white solid having a melting point of 188° C.

$^1$H NMR (δ, DMSO): 1.19 (d, J=6.8 Hz, 6H); 2.60 (m, 4H); 2.67 (s, 3H); 3.19 (m, 4H); 3.32 (m, 2H); 3.40 (m, 1H); 3.56 (m, 1H); 5.68 (s, 2H); 7.22 (d, J=8.7 Hz, 2H); 7.60 (m, 2H); 7.76 (t, J=7.2 Hz, 1H); 7.85 (d, J=8.7 Hz, 2H); 7.98 (d, J=8.3 Hz, 1H); 8.11 (d, J=8 Hz, 1H); 8.34 (m, 1H); 8.89 (m, 1H); 10.62 (m, 1H).

Example 24

N—[(S)-2-Hydroxycarbamoyl-2-(4-methane-sulphonylpiperazin-1-yl)ethyl]-4-(2-methylquinolin-4-ylmethoxy)benzamide dihydrochloride 300 µl of a 5/6N solution of hydrochloric acid in isopropanol are added to a solution of 300 mg (0.6 mmol) of N—[(S)-2-hydroxycarbamoyl-2-(4-methane-sulphonylpiperazin-1-yl)ethyl]-4-(2-methylquinolin-4-yl-methoxy)benzamide (prepared as described in example 14.3) in 6 ml of isopropanol. After stirring at ambient temperature for 2 h, the reaction medium is filtered. The solid is rinsed with isopropanol then recrystallized in a water/isopropanol mixture, filtered and dried under vacuum. 261 mg (34%) of N—[(S)-2-hydroxycarbamoyl-2-(4-methanesulphonylpiperazin-1-yl)-ethyl]-4-(2-methylquinolin-4-ylmethoxy)benzamide dihydrochloride are obtained in the form of a white solid.

$^1$H NMR (δ, CD$_3$OD): 2.87 (s, 3H); 2.95-3.00 (m, 4H); 3.05 (s, 3H); 3.30 (m, 4H); 3.55 (m, 1H); 3.72 (m, 1H); 3.85 (m, 1H); 5.98 (s, 2H); 7.30 (d, J=8 Hz, 2H); 7.90 (m, 2H); 8.00 (m, 1H); 8.20 (m, 3H); 8.48 (d, J=8.5 Hz, 1H).

Example 25

N—[(S)-2-(4-Ethylpiperazin-1-yl)-2-hydroxycarbamoylethyl]-4-(2-methylquinolin-4-ylmethoxy)-benzamide 25-1: Bis(2-chloroethyl)ethylamine 24 ml (330 mmol) of thionyl chloride are added to a solution of 20 g (150 mmol) of 2-[ethyl-(2-hydroxy-ethyl)amino] ethanol in 200 ml of dichloromethane cooled to 0° C. The reaction medium is stirred at ambient temperature for 20 h. After addition of 50 ml of water then gradual addition of a saturated aqueous solution of sodium hydrogen carbonate up to a pH of 7, the reaction medium is extracted with dichloromethane. The organic phase is washed with water, dried over magnesium sulphate, filtered and concentrated under vacuum. 19.5 g (76%) of bis(2-chloroethyl)ethylamine are obtained in the form of a brown oil.

25-2: Methyl (S)-3-tert-butoxycarbonylamino-2-(4-ethylpiperazin-1-yl)propanoate

In a manner similar to example 2-2, starting from 5 g (19.6 mmol) of methyl (S)-2-amino-3-tert-butoxycarbonylaminopropanoate hydrochloride and from 3.3 g (19.6 mmol) of bis(2-chloroethyl)ethylamine, 2.5 g (40%) of methyl (S)-3-tert-butoxycarbonylamino-2-(4-ethylpiperazin-1-yl)propanoate are obtained in the form of light-brown oil.

25-3: Methyl (S)-3-amino-2-(4-ethylpiperazin-1-yl)-propanoate trihydrochloride

In a manner similar to example 2-3, starting from 2.5 g (7.9 mmol) of methyl (S)-3-tert-butoxycarbonylamino-2-(4-eth-ylpiperazin-1-yl)propanoate, 1.4 g (54%) of methyl (S)-3-amino-2-(4-ethylpiperazin-1-yl)propanoate trihydrochloride are obtained in the form of a beige solid.

25-4: Benzyl 4-(2-methylquinolin-4-ylmethoxy)benzoate 3.6 g (26.3 mmol) of potassium carbonate, 5 g (21.9 mmol) of 4-chloromethyl-2-methylquinoline hydrochloride and 5.2 g (23 mmol) of benzyl 4-hydroxybenzoate are put into solution in 30 ml of dimethylformamide. The reaction medium is heated at 60° C. for 18 h then water is added. After extracting with ethyl acetate, the organic phase is washed with water then with a saturated aqueous solution of sodium chloride, dried over magnesium sulphate, filtered and concentrated under vacuum. The crude product is purified by chromatography over silica gel eluted with a 70/30 heptane/ethyl acetate mixture. 3.6 g (43%) of benzyl 4-(2-methylquinolin-4-yl-methoxy)benzoate are obtained in the form of a light-yellow solid.

25-5: 4-(2-Methylquinolin-4-ylmethoxy)benzoic acid 2.3 ml (18.6 mmol) of an 8N aqueous solution of sodium hydroxide and 5 ml of water are added to a solution of 3.6 g (9.3 mmol) of benzyl 4-(2-methylquinolin-4-ylmethoxy) benzoate diluted in 20 ml of tetrahydrofuran and 30 ml of methanol. The reaction medium is stirred at ambient temperature for 48 h then 1 ml of an 8N aqueous solution of sodium hydroxide is added and the mixture is heated at 70° C. for 5 h. After evaporation of the tetrahydrofuran, water and a 1N aqueous solution of acetic acid are added. The suspension is stirred overnight at ambient temperature then filtered. The solid obtained is dried under vacuum at 40° C. for 6 h. 2.2 g (81%) of 4-(2-methylquinolin-4-ylmethoxy)benzoic acid are obtained in the form of a white solid.

25-6: Methyl (S)-2-(4-ethylpiperazin-1-yl)-3-[4-(2-methylquinolin-4-ylmethoxy)benzoylamino]propanoate 0.6 g (2.1 mmol) of 4-(2-methylquinolin-4-ylmethoxy) benzoic acid are dissolved in 10 ml of dimethylformamide then 0.7 g (2.3 mmol) of O-(benzotriazol-1-yl)-N,N,N',N'-tetramethyluronium tetrafluoroborate and 1.1 ml (6.3 mmol) of diisopropylethylamine are added. After stirring for 15 minutes at ambient temperature, a solution of 700 mg (2.1 mmol) of methyl 3-amino-2-(4-ethylpiperazin-1-yl)propanoate trihydrochloride and 1.1 ml (6.3 mmol) of diisopropylethylamine in 10 ml of dimethylformamide is added. The reaction medium is stirred at ambient temperature for 18 h then is hydrolysed with a saturated aqueous solution of sodium hydrogen carbonate. After extraction with ethyl acetate, the organic phase is washed with a saturated aqueous solution of sodium hydrogen carbonate then with a saturated aqueous solution of sodium chloride, dried over magnesium sulphate, filtered and concentrated under vacuum. The product is purified by chromatography over silica gel eluted with a 93/7 dichloromethane/methanol mixture to give 840 mg (81%) of methyl (S)-2-(4-ethylpiperazin-1-yl)-3-[4-(2-methylquinolin-4-ylmethoxy)benzoylamino]propanoate in the form of a colourless oil.

25-7: (S)-2-(4-Ethylpiperazin-1-yl)-3-[4-(2-methylquinolin-4-ylmethoxy)benzoylamino]propanoic acid In a manner similar to example 2-5, starting from 800 mg (1.7 mmol) of methyl (S)-2-(4-ethylpiperazin-1-yl)-3-[4-(2- methylquinolin-4-ylmethoxy)benzoylamino]-propanoate, 780 mg (96%) of (S)-2-(4-ethylpiperazin-1-yl)-3-[4-(2-methylquinolin-4-ylmethoxy)benzoylamino]-propanoic acid are obtained in the form of a beige solid.

25-8: N—[(S)-2-(4-Ethylpiperazin-1-yl)-2-hydroxy-carbamoylethyl]-4-(2-methylquinolin-4-ylmethoxy)-benzamide In a manner similar to example 2-6, starting from 800 mg (1.6 mmol) of (S)-2-(4-ethylpiperazin-1-yl)-3-[4-(2-methylquinolin-4-ylmethoxy)benzoylamino]propanoic acid, 30 mg (4%) of N—[(S)-2-(4-ethylpiperazin-1-yl)-2-hydroxycarbamoylethyl]-4-(2-methylquinolin-4-yl-methoxy)benzamide are obtained in the form of a beige solid having a melting point of 184° C.
$^1$H NMR (δ, DMSO): 0.97 (t, J=7 Hz, 3H); 2.32 (m, 4H); 2.58 (m, 4H); 2.66 (s, 3H); 3.24 (t, J=6.9 Hz, 1H); 3.34 (m, 2H); 3.40 (m, 1H); 3.56 (m, 1H); 5.68 (s, 2H); 7.21 (d, J=8.8 Hz, 2H); 7.59 (m, 2H); 7.75 (t, J=7.2 Hz, 1H); 7.84 (d, J=8.7 Hz, 2H); 7.97 (d, J=8 Hz, 1H); 8.11 (d, J=8 Hz, 1H); 8.28 (s, 1H); 8.85 (s, 1H), 10.58 (s, 1H).

Example 26

N-{(S)-2-[4-(4-Fluoro-benzyl)piperazin-1-yl]-2-hydroxycarbamoylethyl}-4-(2-methylquinolin-4-yl-methoxy)benzamide 26-1: Bis(2-chloroethyl)(4-fluorobenzyl)amine 8.5 g (61.6 mmol) of potassium carbonate and 3.8 ml (30.8 mmol) of 1-bromomethyl-4-fluorobenzene are added to a solution of 5 g (28 mmol) of 2-[ethyl-(2-hydroxyethyl) amino]ethanol in 80 ml of acetonitrile. The mixture is heated for 5 h at 60° C. then filtered and concentrated under vacuum. 6.9 g (100%) of bis(2-chloroethyl)(4-fluorobenzyl)amine are obtained in the form of a colourless oil.

26-2: Methyl (S)-3-tert-butoxycarbonylamino-2-[4-(4-fluorobenzyl)piperazin-1-yl]propanoate In a manner similar to example 2-2, starting from 7.1 g (28 mmol) of commercial methyl (S)-2-amino-3-tert-butoxycarbonylaminopropanoate hydrochloride and from 6.9 g (28 mmol) of bis(2-chloroethyl)(4-fluorobenzyl)-amine, 5.3 g (48%) of methyl (S)-3-tert-butoxycarbonylamino-2-[4-(4-fluorobenzyl)piperazin-1-yl]propanoate are obtained in the form of a light-brown oil.

26-3: Methyl (S)-3-amino-2-[4-(4-fluorobenzyl)-piperazin-1-yl]propanoate trihydrochloride In a manner similar to example 2-3, starting from 5.3 g (13.4 mmol) of methyl (S)-3-tert-butoxycarbonylamino-2-(4-ethylpiperazin-1-yl)propanoate, 5.4 g (100%) of (S)-3-amino-2-[4-(4-fluorobenzyl)piperazin-1-yl]propanoate trihydrochloride are obtained in the form of a beige solid.

26-4: Methyl (S)-2-(4-fluorobenzylpiperazin-1-yl)-3-[4-(2-methylquinolin-4-ylmethoxy)benzoylamino] propanoate In a manner similar to example 25-6, starting from 1.1 g (3.7 mmol) of 4-(2-methylquinolin-4-ylmethoxy)-benzoic acid (prepared as described in 25-5) and from 1.5 g (3.7 mmol) of methyl (S)-3-amino-2-(4-fluorobenzylpiperazin-1-yl)propanoate trihydrochloride, 1.7 g (80%) of methyl (S)-2-(4-fluorobenzylpiperazin-1-yl)-3-[4-(2-methylquinolin-4-ylmethoxy)benzoylamino]-propanoate are obtained in the form of a yellow oil.

26-5: (S)-2-[4-(4-Fluorobenzyl)piperazin-1-yl]-3-[4-(2-methylquinolin-4-ylmethoxy)benzoylamino]propanoic acid In a manner similar to example 2-5, starting from 1.7 g (3 mmol) of methyl (S)-2-(4-fluorobenzylpiperazin-1-yl)-3-[4-(2-methylquinolin-4-ylmethoxy)benzoylamino]-propanoate, 1.4 g (87%) of (S)-2-[4-(4-fluoro-benzyl)piperazin-1-yl]-3-[4-(2-methylquinolin-4-ylmethoxy)-benzoylamino] propanoic acid are obtained in the form of a beige solid.

26-6: N-{(S)-2-[4-(4-Fluorobenzyl)piperazin-1-yl]-2-hydroxycarbamoylethyl}-4-(2-methylquinolin-4-yl-methoxy)benzamide In a manner similar to example 2-6, starting from 1.5 g (2.6 mmol) of (S)-2-[4-(4-fluorobenzyl)piperazin-1-yl]-3-[4-(2-methylquinolin-4-ylmethoxy)benzoylamino]-propanoic acid, 450 mg (30%) of N-{(S)-2-[4-(4-fluorobenzyl)piperazin-1-yl]-2-hydroxycarbamoylethyl}-4-(2-methylquinolin-4-ylmethoxy)benzamide are obtained in the form of a beige solid having a melting point of 167° C.
$^1$H NMR (δ, DMSO): 2.32 (m, 4H); 2.57 (m, 4H); 2.66 (s, 3H); 3.23 (t, J=7 Hz, 1H); 3.34 (s, 2H); 3.39 (m, 1H); 3.54 (m, 1H); 5.68 (s, 2H); 7.12 (t, J=8.8 Hz, 2H); 7.21 (d, J=8.9 Hz, 2H); 7.30 (m, 2H); 7.59 (m, 2H); 7.75 (m, 1H); 7.83 (d, J=8.8 Hz, 2H); 7.97 (d, J=8.2 Hz, 1H); 8.11 (d, J=8 Hz, 1H); 8.26 (t, J=5.3 Hz, 1H); 8.84 (s, 1H); 10.55 (s, 1H).

Example 27

N-[2-(4-Benzylpiperazin-1-yl)-2-hydroxycarbamoyl-ethyl]-4-(2-trifluoromethylpyrazolo[1,5-a]pyridin-3-ylmethoxy)benzamide 27-1: Ethyl 2-trifluoromethylpyrazolo[1,5-a]pyridine-3-carboxylate A mixture of 2.1 g (37.6 mmol) of potassium hydroxide and 6.7 g (30.1 mmol) of aminopyridinium iodide in 20 ml of water is added to a solution of 2.5 g (15.1 mmol) of ethyl 4,4,4-trifluorobut-2-ynoate in 25 ml of dichloromethane. After stirring for 5 h at ambient temperature, water is added and the mixture is extracted with dichloromethane. The organic phase is washed with water, dried over magnesium sulphate, filtered and concentrated to dryness. The crude product is purified by chromatography over silica gel eluted with an 80/20 heptane/ethyl acetate mixture. 2.8 g (73%) of ethyl 2-trifluoromethylpyrazolo[1,5-a]pyridine-3-carboxylate are obtained in the form of a yellow solid.

27-2: (2-Trifluoromethylpyrazolo[1,5-a]pyridin-3-yl)-methanol

A solution of 2.8 g (10.8 mmol) of ethyl 2-trifluoromethylpyrazolo[1,5-a]pyridine-3-carboxylate in 50 ml of tetrahydrofuran is added dropwise to a mixture of 0.5 g (11.9 mmol) of lithium aluminium hydride in suspension in 45 ml of tetrahydrofuran at −70° C. After stirring for 3 h at −70° C., the mixture is brought to ambient temperature, then 1.8 ml of a 2N aqueous sodium hydroxide solution is added. The mixture is filtered, dried over magnesium sulphate, filtered and concentrated. 2.3 g (100%) of (2-trifluoromethylpyrazolo[1,5-a]pyridin-3-yl)methanol are obtained in the form of a yellow solid.

27-3: Methyl (S)-2-(4-benzylpiperazin-1-yl)-3-[4-(2-trifluoromethylpyrazolo[1,5-a]pyridin-3-ylmethoxy)-benzoylamino]propanoate 795 mg (3.0 mmol) of triphenylphosphine and 565 mg (2.6 mmol) of (2-trifluoromethylpyrazolo[1,5-a]pyridin-3-yl) methanol are added respectively to a solution of 800 mg (2.0 mmol) of methyl (S)-2-(4-benzylpiperazin-1-yl)-3-(4-hydroxybenzoylamino)propanoate (prepared as described in example 22-5) in 8 ml of tetrahydrofuran. After stirring at ambient temperature for 30 min, 595 µl (3.0 mmol) of diisopropyl azodicarboxylate are added and the medium is stirred for 18 h at ambient temperature. After evaporating to dryness, the crude residue obtained is purified by chromatography over a silica column eluted with 100% ethyl acetate. 590 mg (49%) of methyl (S)-2-(4-benzylpiperazin-1-yl)-3-[4-(2-trifluoromethylpyrazolo[1,5-a]pyridin-3-ylmethoxy)-benzoylamino]propanoate are obtained in the form of a light-yellow solid.

27-4: 2-(4-Benzylpiperazin-1-yl)-3-[4-(2-trifluoromethylpyrazolo[1,5-a]pyridin-3-ylmethoxy)benzoylamino]-propanoic acid In a manner similar to example 2-5, starting from 590 mg (0.7 mmol) of methyl (S)-2-(4-benzylpiperazin-1-yl)-3-[4-(2-trifluoromethylpyrazolo[1,5-a]pyridin-3-yl-methoxy)benzoylamino]propanoate, 190 mg (47%) of 2-(4-benzylpiperazin-1-yl)-3-[4-(2-trifluoromethylpyrazolo-[1,5-a]pyridin-3-ylmethoxy)benzoylamino]propanoic acid are obtained in the form of a white solid.

27-5: N-[2-(4-Benzylpiperazin-1-yl)-2-hydroxycarbamoyl-ethyl]-4-(2-trifluoromethylpyrazolo[1,5-a]-pyridin-3-ylmethoxy)benzamide 106 g (0.3 mmol) of O-(benzotriazol-1-yl)-N,N,N',N'-tetramethyluronium tetrafluoroborate and 0.2 ml (1.2 mmol) of diisopropylethylamine are added to a solution of 190 mg (0.3 mmol) of 2-(4-benzylpiperazin-1-yl)-3-[4-(2-trifluoromethylpyrazolo[1,5-a]pyridin-3-ylmethoxy)benzoylamino]propanoic acid in 10 ml of dimethylformamide. After stirring for 20 minutes at ambient temperature, 53 mg (0.4 mmol) of O-tert-butyldimethylsilylhydroxylamine diluted in 3 ml of dimethylformamide are added. The reaction medium is stirred at ambient temperature for 18 h, then hydrolysed with 1 ml of a 5% aqueous solution of citric acid and 2 ml of water and stirred for 1 h. The mixture is then brought to pH=8 with a saturated aqueous solution of sodium hydrogen carbonate then extracted with ethyl acetate. The organic phase is washed with a saturated aqueous solution of sodium hydrogen carbonate then with a saturated aqueous solution of sodium chloride, dried over magnesium sulphate, filtered and concentrated under vacuum. The crude product obtained is precipitated in a heptane/ethyl acetate mixture then filtered. The solid obtained is recrystallized in ethyl acetate. 41 mg (21%) of N-[2-(4-benzylpiperazin-1-yl)-2-hydroxycarbamoyl-ethyl]-4-(2-trifluoromethylpyrazolo-[1,5-a]-pyridin-3-ylmethoxy)benzamide are obtained in the form of a white solid.

$^1$H NMR (δ, DMSO): 2.38 (m, 4H); 2.61 (m, 4H); 3.25 (m, 2H); 3.39 (m, 2H); 3.52 (m, 1H); 5.42 (s, 2H); 7.10 (d, J=8.8 Hz, 2H); 7.18 (t, J=1.2 Hz, 1H); 7.31 (m, 5H); 7.50 (m, 1H); 7.80 (d, J=8.8 Hz, 2H); 8.05 (d, J=9 Hz, 1H); 8.25 (m, 1H); 8.86 (m, 2H), 10.57 (m, 1H).

Example 28

Enzymatic Test of TACE Inhibition

Description of the Test

The products are dissolved in DMSO at a concentration of 10 mM. A 3-fold serial dilution is carried out over 10 steps so as to have a concentration range going from 10 µM to a final concentration of 0.5 nM.

The TACE enzyme is an internal production (carried out according to the publication "Protein Eng Des Sel, 2006, 19, 155-161") and is added so as to have a signal equivalent to 6 times the background noise over 2 h at 37° C. The reaction takes place in a buffered medium: Tris 50 mM, 4% of glycerol, pH 7.4. The fluorescent substrate is MCA-Pro-Leu-Ala-Val-(Dpa)-Arg-Ser-Ser-Arg-NH2 (R&D system reference: ES003). The substrate is cleaved by the enzyme between alanine and valine thus releasing a fluorescent peptide (excitation: 320 nm, emission: 420 nm). The substrate is used at 40 µM. The reaction is carried out in a final volume of 10 µl (4 µl inhibitor, 4 µl substrate, 2 µl enzyme) in a plate of 384 low-volume wells (Corning reference: 3676). The plate is incubated for 2 h at ambient temperature, then read in fluorescence mode using a Pherastar (BMG labtech). The $IC_{50}$ values are determined using mathematical processing software (XLfit).

Test of the Products

| Example No. | % TACE inhibition at 10 µM | $IC_{50}$ - TACE (nM) |
|---|---|---|
| Ex1 | 100 | 32 |
| Ex2 | 100 | 28 |
| Ex4 | 100 | 160 |
| Ex5 | 100 | 200 |
| Ex6 | 100 | 40 |
| Ex8 | 100 | 54 |
| Ex9 | 98 | 21 |
| Ex10 | 97 | 117 |
| Ex11 | 96 | 95 |
| Ex13 | 98 | 22 |
| Ex14 | 98 | 35 |
| Ex16 | 97 | 35 |
| Ex17 | 98 | 70 |
| Ex18 | 98 | 99 |
| Ex19 | 90 | 138 |
| Ex21 | 96 | 118 |
| Ex22 | 97 | 79 |
| Ex23 | 97 | 102 |
| Ex24 | 98 | 88 |
| Ex25 | 90 | 45 |
| Ex27 | 95 | 81 |

On the basis of the results obtained in the enzymatic TACE test described above, the compounds claimed in the present invention are TNF-alpha converting enzyme (TACE) inhibitors and therefore may be potential active principles for the treatment of pathologies for which reducing TNF-alpha production would be of great benefit.

Example 29

Selectivity Test

Test Principle:
The molecules are tested in dose-response studies on the following enzymes MMP1, MMP3, MMP9, ADAMS and ADAM10 according to the same protocol as that described for the TACE enzyme in example 28 but with different substrates (MMP R&D system reference: P126-990 and ADAM R&D system reference: ES003).
The enzymes are purchased from Calbiochem.
Test of the Products:

| | $IC_{50}$ (nM) | | | | | |
|---|---|---|---|---|---|---|
| Example | MMP1 | MMP3 | MMP9 | ADAM9 | ADAM10 | TACE |
| 2 | >10000 | 6306 | >10000 | 3251 | 942 | 28 |
| 14 | 2605 | 6827 | >10000 | >10000 | 5795 | 35 |
| 27 | >10000 | >10000 | >10000 | >10000 | >10000 | 81 |
| Apratastat | 145 | 10 | 82 | 85 | 71 | 5 |

On the basis of the results obtained in the selectivity test described above, these compounds are also highly selective for TACE compared to other ADAMs and MMPs, that is to say that they have $IC_{50}$ values for other ADAMs or MMPs at least 10 times greater than that obtained for TACE, and more advantageously at least 100 times greater.

However, in so far as it is known that the non-selective inhibition of these families of enzymes induces undesirable side effects observed in vivo, the selective inhibition of TACE compared to these other enzymes should make it possible to reduce undesirable side effects during the administration of these molecules for the treatment of pathologies for which reducing TNF-alpha production would be of great benefit.

The invention claimed is:
1. A compound of formula (I) below;

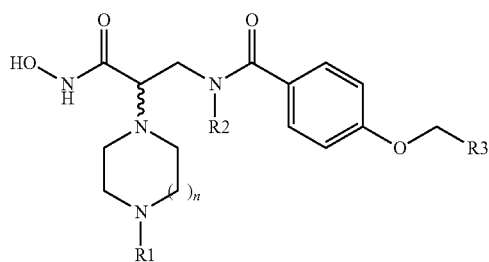

(I)

in which:
R₁ is a hydrogen atom; an alkyl radical comprising from 1 to 10 carbon atoms; an alkyl radical substituted with one or more radicals selected from the group consisting of a halogen atom, an alkoxy radical, and a hydroxyl radical; an alkenyl radical comprising from 2 to 10 carbon atoms; an alkenyl radical substituted with one or more radicals selected from the group consisting of a halogen atom, an alkoxy radical, and a hydroxyl radical; an alkynyl radical comprising from 2 to 10 carbon atoms; an alkynyl radical substituted with one or more radicals selected from the group consisting of a halogen atom, an alkoxy radical, and a hydroxyl radical; an aralkyl radical; a substituted aralkyl radical; a heteroaralkyl radical; a heteroaralkyl radical substituted with one or more radicals selected from the group consisting of an alkyl, an alkoxy, an aryl, a halogen, a hydroxyl, a cyano, a trifluoromethyl, and a nitro; a —C(O)—R₄ radical; an —SO₂—R₄ radical; or a C(O)OR₄ radical; with R₄ having the meanings given below;

R₂ is a hydrogen atom; or a lower alkyl radical comprising from 1 to 4 carbon atoms;

R₃ is an alkyl radical comprising from 1 to 10 carbon atoms; an alkyl radical substituted with one or more radicals selected from the group consisting of a halogen atom, an alkoxy radical, and a hydroxyl radical; an alkenyl radical comprising from 2 to 10 carbon atoms; an alkenyl radical substituted with one or more radicals chosen from a halogen atom, an alkoxy radical, and a hydroxyl radical; an alkynyl radical comprising from 2 to 10 carbon atoms; an alkynyl radical substituted with one or more radicals selected from the group consisting of a halogen atom, an alkoxy radical, and a hydroxyl radical; an aryl radical; an aryl radical substituted with one or more radicals selected from the group consisting of an alkyl, an alkoxy, an aryl, a halogen, a hydroxyl, a cyano, a trifluoromethyl, and a nitro; an aralkyl radical; a substituted aralkyl radical; a heterocyclic radical; a heterocyclic, radical substituted with one or more radicals selected from the group consisting of an alkyl, an alkoxy, a halogen, a hydroxyl, a cyano, a trifluoromethyl, and a nitro; a cycloalkyl radical; a cycloalkyl radical substituted with one or more radicals selected from the group consisting of a halogen atom, an alkoxy radical, and a hydroxyl radical; a heteroaralkyl radical; or a heteroaralkyl radical substituted with one or more radicals selected from the group consisting of an alkyl, an alkoxy, a halogen, a hydroxyl, a cyano, a trifluoromethyl, and a nitro;

R₄ is an alkyl radical comprising from 1 to 10 carbon atoms; an alkyl radical substituted with one or more radicals selected from the group consisting of a halogen atom, an alkoxy radical, and a hydroxyl radical; an alkenyl radical comprising from 2 to 10 carbon atoms; an alkenyl radical substituted with one or more radicals selected from the group consisting of a halogen atom, an alkoxy radical, and a hydroxyl radical; an alkynyl radical comprising from 2 to 10 carbon atoms; an alkynyl radical substituted with one or more radicals selected from the group consisting of a halogen atom, an alkoxy radical, and a hydroxyl radical; an aryl radical; an aryl radical substituted with one or more radicals selected from the group consisting of an alkyl, an alkoxy, an aryl, a halogen, a hydroxyl, a cyano, a trifluoromethyl, and a nitro; an aralkyl radical; or a substituted aralkyl radical; and n takes the values of 0, 1, 2, or 3;

or an addition salt of the compound of formula (I) with a pharmaceutically acceptable acid; an addition salt of the compound of formula (I) with a pharmaceutically acceptable base; or an enantiomer of the compound of formula (I).

2. The addition salt of the compound according to claim 1, with a pharmaceutically acceptable acid, wherein the pharmaceutically acceptable acid is selected from the group consisting of hydrochloric acid, hydrobromic acid, sulphuric acid, nitric acid, phosphoric acid, acetic acid, trifluoroacetic acid, trichloroacetic acid, propionic acid, glycolic acid, pyruvic acid, succinic acid, benzoic acid, cinnamic acid, mandelic acid, methanesulphonic acid, para-toluenesulphonic acid, salicylic acid, picric acid, citric acid, oxalic acid, tartaric acid, malonic acid, maleic acid, camphorsulphonic acid, and fumaric acid.

3. The addition salt of the compound according to claim 1, with a pharmaceutically acceptable base, wherein the pharmaceutically acceptable base is selected from the group consisting of potassium hydroxide, sodium hydroxide, lithium hydroxide, calcium hydroxide, potassium carbonate, sodium carbonate, calcium carbonate, methylamine, ethylamine, ethanolamine, propylamine, isopropylamine, the 4 isomers of butylamine, dimethylamine, diethylamine, diethanolamine, dipropylamine, diisopropylamine, di-n-butylamine, pyrrolidine, piperidine, morpholine, diethanolphenylamine, trimethylamine, triethylamine, tripropylamine, quinuclidine, pyridine, quinoline, isoquinoline, lysine, arginine, and ornithine.

4. The compound according to claim 1, wherein:
$R_1$ is a hydrogen atom; an alkyl radical; a substituted alkyl radical; an alkenyl radical; a substituted alkenyl radical; an alkynyl radical; a substituted alkynyl radical; an aralkyl radical; a substituted aralkyl radical; a heteroaralkyl radical; a substituted heteroaralkyl radical; a —C(O)—$R_4$ radical; an —SO$_2$—$R_4$ radical; or a C(O)OR$_4$ radical; with $R_4$ having the meanings given below;
$R_2$ is a hydrogen atom; or a lower alkyl radical;
$R_3$ is an alkyl radical; a substituted alkyl radical; an alkenyl radical; a substituted alkenyl radical; an alkynyl radical; a substituted alkynyl radical; an aryl radical; a substituted aryl radical; an aralkyl radical; a substituted aralkyl radical; a heterocyclic radical; a substituted heterocyclic radical; a heteroaralkyl radical; or a substituted heteroaralkyl radical;
$R_4$ is an alkyl radical; a substituted alkyl radical; an alkenyl radical; a substituted alkenyl radical; an alkynyl radical; a substituted alkynyl radical; an aryl radical; a substituted aryl radical; an aralkyl radical; or a substituted aralkyl radical; and
n takes the values of 0, 1, or 2;
or an addition salt of the compound with a pharmaceutically acceptable acid; an addition salt of the compound with a pharmaceutically acceptable base; or an enantiomer of the compound.

5. The compound according to claim 1, wherein:
$R_1$ is a hydrogen atom; an alkyl radical; a substituted alkyl radical; an alkenyl radical; a substituted alkenyl radical; an alkynyl radical; a substituted alkynyl radical; an aralkyl radical; a substituted aralkyl radical; a —C(O)—$R_4$ radical; or an —SO$_2$—$R_4$ radical; with $R_4$ having the meanings given below;
$R_2$ is a hydrogen atom; or a lower alkyl radical;
$R_3$ is an alkyl radical; a substituted alkyl radical; an alkenyl radical; a substituted alkenyl radical; an alkynyl radical; a substituted alkynyl radical; an aryl radical; a substituted aryl radical; an aralkyl radical; a substituted aralkyl radical; a heterocyclic radical; a substituted heterocyclic radical; a heteroaralkyl radical; or a substituted heteroaralkyl radical;
$R_4$ is an alkyl radical; a substituted alkyl radical; an aryl radical; a substituted aryl radical; an aralkyl radical; or a substituted aralkyl radical; and
n takes the values of 1 or 2;
or an addition salt of the compound with a pharmaceutically acceptable acid; an addition salt of the compound with a pharmaceutically acceptable base; or an enantiomer of the compound.

6. The compound according to claim 1, wherein:
$R_1$ is an alkyl radical; a substituted alkyl radical; an aralkyl radical; a substituted aralkyl radical; a —C(O)—$R_4$ radical; or an —SO$_2$—$R_4$ radical; with $R_4$ having the meanings given below;
$R_2$ is a hydrogen atom;
$R_3$ is an alkynyl radical; a substituted alkynyl radical; an aryl radical; a substituted aryl radical; an aralkyl radical; a substituted aralkyl radical; a heterocyclic radical; a substituted heterocyclic radical; a heteroaralkyl radical; or a substituted heteroaralkyl radical;
$R_4$ is an alkyl radical; a substituted alkyl radical; an aryl radical; a substituted aryl radical; an aralkyl radical; or a substituted aralkyl radical; and
n takes the value of 1;
or an addition salt of the compound with a pharmaceutically acceptable acid; an addition salt of the compound with a pharmaceutically acceptable base; or an enantiomer of the compound.

7. The compound according to claim 1, wherein:
$R_1$ is an alkyl radical; a substituted alkyl radical; an aralkyl radical; a substituted aralkyl radical; a —C(O)—$R_4$ radical; or an —SO$_2$—$R_4$ radical; with $R_4$ having the meanings given below;
$R_2$ is a hydrogen atom;
$R_3$ is an alkynyl radical; a substituted alkynyl radical; a heterocyclic radical; a substituted heterocyclic radical; a heteroaralkyl radical; or a substituted heteroaralkyl radical;
$R_4$ is an alkyl radical; a substituted alkyl radical; an aryl radical; a substituted aryl radical; an aralkyl radical; or a substituted aralkyl radical; and
n takes the value of 1;
or an addition salt of the compound with a pharmaceutically acceptable acid; an addition salt of the compound with a pharmaceutically acceptable base; or an enantiomer of the compounds.

8. A compound selected from the group consisting of:
1) 4-but-2-ynyloxy-N-[2-hydroxycarbamoyl-2-(4-methanesulphonylpiperazin-1-yl)ethyl]benzamide;
2) 4-but-2-ynyloxy-N—[(S)-2-hydroxycarbamoyl-2-(4-methanesulphonylpiperazin-1-yl)ethyl]benzamide;
3) 4-but-2-ynyloxy-N—[(R)-2-hydroxycarbamoyl-2-(4-methanesulphonylpiperazin-1-yl)ethyl]benzamide;
4) N—[(S)-2-hydroxycarbamoyl-2-(4-methanesulphonylpiperazin-1-yl)ethyl]-4-methoxybenzamide;
5) 4-cyclopropylmethoxy-N—[(S)-2-hydroxycarbamoyl-2-(4-methanesulphonylpiperazin-1-yl)ethyl]benzamide;
6) 4-benzyloxy-N—[(S)-2-hydroxycarbamoyl-2-(4-methanesulphonylpiperazin-1-yl)ethyl]benzamide;
7) 4-butoxy-N—[(S)-2-hydroxycarbamoyl-2-(4-methanesulphonylpiperazin-1-yl)ethyl]benzamide;
8) 4-but-2-ynyloxy-N—{(S)-2-hydroxycarbamoyl-2-[4-(toluene-4-sulphonyl)piperazin-1-yl]ethyl}-benzamide;
9) 4-(4-fluorobenzyloxy)-N—[(S)-2-hydroxycarbamoyl-2-(4-methanesulphonylpiperazin-1-yl)ethyl]benzamide hydrochloride;
10) N—[(S)-2-hydroxycarbamoyl-2-(4-methanesulphonylpiperazin-1-yl)ethyl]-4-(4-trifluoromethyl-benzyloxy)benzamide;
11) N—[(S)-2-hydroxycarbamoyl-2-(4-methanesulphonylpiperazin-1-yl)ethyl]-4-(4-methylbenzyloxy)-benzamide;

12) [(S)-2-hydroxycarbamoyl-2-(4-methanesulphonylpiperazin-1-yl)ethyl]-2,3-dihydrobenzofuran-5-carboxamide;
13) 4-but-2-ynyloxy-N—[(S)-2-hydroxycarbamoyl-2-(4-methanesulphonylpiperazin-1-yl)ethyl]-N-methyl-benzamide;
14) N—[(S)-2-hydroxycarbamoyl-2-(4-methanesulphonylpiperazin-1-yl)ethyl]-4-(2-methylquinolin-4-yl-methoxy)benzamide;
15) N—[(S)-2-hydroxycarbamoyl-2-(4-methanesulphonylpiperazin-1-yl)ethyl]-4-(naphthalen-1-ylmethoxy)-benzamide;
16) 4-(4-hydroxybut-2-ynyloxy)-N—[(S)-2-hydroxycarbamoyl-2-(4-methanesulphonylpiperazin-1-yl)-ethyl]benzamide;
17) N—[(S)-2-hydroxycarbamoyl-2-(4-methanesulphonylpiperazin-1-yl)ethyl]-4-(4-methoxybenzyloxy)-benzamide;
18) N—[(S)-2-hydroxycarbamoyl-2-(4-methanesulphonylpiperazin-1-yl)ethyl]-4-(pyridin-4-ylmethoxy)-benzamide;
19) N—[(S)-2-hydroxycarbamoyl-2-(4-methanesulphonylpiperazin-1-yl)ethyl]-4-(2-methylnaphthalen-1-yl-methoxy)benzamide;
20) N—[(R)-2-hydroxycarbamoyl-2-(4-methanesulphonylpiperazin-1-yl)ethyl]-4-(2-methylquinolin-4-yl-methoxy)benzamide;
21) N—[(S)-2-hydroxycarbamoyl-2-(4-methanesulphonylpiperazin-1-yl)ethyl]-4-(quinolin-4-ylmethoxy)-benzamide;
22) N—[(S)-2-(4-benzylpiperazin-1-yl)-2-hydroxycarbamoylethyl]-4-(2-methylquinolin-4-ylmethoxy)-benzamide:
23) N-{(S)-2-hydroxycarbamoyl-2-[4-(propane-2-sulphonyl)piperazin-1-yl]ethyl}-4-(2-methylquinolin-4-yl-methoxy)benzamide;
24) N—[(S)-2-hydroxycarbamoyl-2-(4-methanesulphonylpiperazin-1-yl)ethyl]-4-(2-methylquinolin-4-yl-methoxy)benzamide dihydrochloride;
25) N—[(S)-2-(4-ethylpiperazin-1-yl)-2-hydroxycarbamoylethyl]-4-(2-methylquinolin-4-ylmethoxy)-benzamide;
26) N—{(S)-2-[4-(4-fluorobenzyl)piperazin-1-yl]-2-hydroxycarbamoylethyl}-4-(2-methylquinolin-4-yl-methoxy)benzamide;
27) N—[(S)-2-(4-benzylpiperazin-1-yl)-2-hydroxycarbamoylethyl]-4-(2-trifluoromethylpyrazolo[1,5-a]pyridin-3-ylmethoxy)benzamide;
28) N—[(S)-2-hydroxycarbamoyl-2-[4-(propane-2-sulphonyl)piperazin-1-yl]ethyl]-4-(1-methylpiperidin-4-ylmethoxy)benzamide;
29) N—[(S)-2-hydroxycarbamoyl-2-(4-isobutyryl-piperazin-1-yl)ethyl]-4-(2-methylpyridin-4-yl-methoxy)-N-propylbenzamide;
30) N—[(S)-2-(3-benzylimidazolidin-1-yl)-2-hydroxycarbamoylethyl]-4-(2,6-dimethylpyridin-4-yl-methoxy)benzamide;
31) N—[(S)-2-hydroxycarbamoyl-2-(3-methanesulphonyl-imidazolidin-1-yl)ethyl]-4-(3-methylbenzyloxy)-benzamide;
32) N—[(S)-2-hydroxycarbamoyl-2-(4-methanesulphonyl-[1,4]diazepan-1-yl)ethyl]-4-(2-methylquinolin-4-ylmethoxy)benzamide;
33) N—((S)-2-[1,4]diazepan-1-yl-2-hydroxycarbamoyl-ethyl)-4-(quinolin-4-ylmethoxy)benzamide;
34) 4-(2-cyclopropylquinolin-4-ylmethoxy)-N—{(S)-2-hydroxycarbamoyl-2-[4-(propane-2-sulphonyl)-piperazin-1-yl]ethyl}benzamide:
35) 4-(2-cyclopropylpyridin-4-ylmethoxy)-N—[(S)-2-(4-ethyl[1,4]diazocan-1-yl)-2-hydroxycarbamoyl-ethyl]-benzamide;
36) N—[(S)-2-hydroxycarbamoyl-2-(4-isobutyryl-[1,4]diazocan-1-yl)ethyl]-4-(2-methylpyrazolo-[1,5-a]pyridin-3-ylmethoxy)benzamide;
37) N—[(S)-2-hydroxycarbamoyl-2-(4-methanesulphonylpiperazin-1-yl)ethyl]-4-(2-trifluoromethylpyrazolo[1,5-a]pyridin-3-ylmethoxy)benzamide;
38) N—[(S)-2-(4-benzenesulphonylpiperazin-1-yl)-2-hydroxycarbamoylethyl]-4-(3-methyl-1i H-pyrazol-4-yl-methoxy)benzamide;
39) N—[(R)-2-(4-benzoylpiperazin-1-yl)-2-hydroxycarbamoylethyl]-4-(piperidin-4-ylmethoxy)-benzamide;
40) N—[(S)-2-hydroxycarbamoyl-2-(4-isobutyryl-piperazin-1-yl)ethyl]-4-(2-methylquinolin-4-yl-methoxy)benzamide;
41) N—{(S)-2-hydroxycarbamoyl-2-[4-(propane-2-sulphonyl)piperazin-1-yl]ethyl}-4-(2-methyl-1H-indol-3-ylmethoxy)benzamide; and
42) N—[(S)-2-(4-benzylpiperazin-1-yl)-2-hydroxycarbamoylethyl]-4-(2-isopropylbenzofuran-3-yl-methoxy)benzamide;

or an addition salt of the compound with a pharmaceutically acceptable acid; or an addition salt of the compound with a pharmaceutically acceptable base.

9. A pharmaceutical composition comprising the compound according to claim 1, addition salt thereof, or enantiomer thereof.

10. A method of inhibiting TNFα secretion, wherein the method comprises administering the pharmaceutical composition according to claim 9 to a cell that secretes TNFα.

11. A method of inhibiting TNFα-converting enzyme (TACE) activity, wherein the method comprises contacting a TACE with the pharmaceutical composition according to claim 9.

12. A method for the treatment of diseases or disorders that involve TNFα production, wherein the method comprises administering the pharmaceutical composition according to claim 9 to a subject in need thereof, wherein the diseases or disorders are selected from the group consisting of Crohn's disease, ulcerative colitis, rheumatoid arthritis, ankylosing spondylitis, chronic juvenile arthritis, non-insulin-dependent diabetes mellitus, psoriasis, atopic dermatitis, and psoriatic arthritis.

13. The compound according to claim 1, wherein the heterocyclic radical is a heteroaryl radical.

14. The compound according to claim 13, wherein:

$R_1$ is an alkyl radical; a substituted alkyl radical; an aralkyl radical; a substituted aralkyl radical; a —C(O)—$R_4$ radical; or an —$SO_2$—$R_4$ radical; with $R_4$ having the meanings given below;

$R_2$ is a hydrogen atom;

$R_3$ is an alkynyl radical; a substituted alkynyl radical; a heteroaryl radical; or a heteroaryl radical substituted with one or more radicals selected from the group consisting of an alkyl, an alkoxy; an aryl, a substituted aryl, a halogen, a hydroxyl, a cyano, a trifluoromethyl, and a nitro;

R$_4$ is an alkyl radical; a substituted alkyl radical; an aryl radical; a substituted aryl radical; an aralkyl radical; or a substituted aralkyl radical; and n takes the value of 1;

or an addition salt of the compound with a pharmaceutically acceptable acid; an addition salt of the compound with a pharmaceutically acceptable base; or an enantiomer of the compound.

15. The compound according to claim 4, wherein the heterocyclic radical is a heteroaryl radical.

16. The compound according to claim 5, wherein the heterocyclic radical is a heteroaryl radical.

17. The compound according to claim 6, wherein the heterocyclic radical is a heteroaryl radical.

18. The compound according to claim 7, wherein the heterocyclic radical is a heteroaryl radical.

19. The compound according to claim 1, wherein the heterocyclic radical substituted with one or more radicals is a heteroaryl radical substituted with one or more radicals selected from the group consisting of an alkyl, an alkoxy, an aryl, a substituted aryl, a halogen, a hydroxyl, a cyano, a trifluoromethyl, and a nitro.

20. The compound according to claim 4, wherein the heterocyclic radical substituted with one or more radicals is a heteroaryl radical substituted with one or more radicals selected from the group consisting of an alkyl, an alkoxy, an aryl, a substituted aryl, a halogen, a hydroxyl, a cyano, a trifluoromethyl, and a nitro.

21. The compound according to claim 5, wherein the heterocyclic radical substituted with one or more radicals is a heteroaryl radical substituted with one or more radicals selected from the group consisting of an alkyl, an alkoxy, an aryl, a substituted aryl, a halogen, a hydroxyl, a cyano, a trifluoromethyl, and a nitro.

22. The compound according to claim 6, wherein the heterocyclic radical substituted with one or more radicals is a heteroaryl radical substituted with one or more radicals selected from the group consisting of an alkyl, an alkoxy, an aryl, a substituted aryl, a halogen, a hydroxyl, a cyano, a trifluoromethyl, and a nitro.

23. The compound according to claim 7, wherein the heterocyclic radical substituted with one or more radicals is a heteroaryl radical substituted with one or more radicals selected from the group consisting of an alkyl, an alkoxy, an aryl, a substituted aryl, a halogen, a hydroxyl, a cyano, a trifluoromethyl, and a nitro.

* * * * *